US009096869B2

(12) United States Patent
Sondermeijer et al.

(10) Patent No.: US 9,096,869 B2
(45) Date of Patent: Aug. 4, 2015

(54) RECOMBINANT NONPATHOGENIC MDV VECTOR PROVIDING MULTIVALENT IMMUNITY

(71) Applicant: Intervet Inc., Summit, NJ (US)

(72) Inventors: Paulus Jacobus Antonius Sondermeijer, Boxmeer (NL); Iwan Verstegen, Boxmeer (NL)

(73) Assignee: Intervet, Inc., Summit, NJ (US)

( * ) Notice: Subject to any disclaimer, the term of this patent is extended or adjusted under 35 U.S.C. 154(b) by 0 days.

(21) Appl. No.: 14/351,739

(22) PCT Filed: Oct. 19, 2012

(86) PCT No.: PCT/EP2012/070727

§ 371 (c)(1),
(2) Date: Apr. 14, 2014

(87) PCT Pub. No.: WO2013/057235

PCT Pub. Date: Apr. 25, 2013

(65) Prior Publication Data

US 2014/0294893 A1 Oct. 2, 2014

(30) Foreign Application Priority Data

Oct. 21, 2011 (EP) .................................... 11186237

(51) Int. Cl.

| | |
|---|---|
| ***A61K 39/17*** | (2006.01) |
| ***A61K 39/255*** | (2006.01) |
| ***C12N 7/01*** | (2006.01) |
| ***C12N 15/869*** | (2006.01) |
| ***C12N 15/86*** | (2006.01) |
| ***A61K 39/12*** | (2006.01) |
| ***C07K 14/005*** | (2006.01) |
| *A61K 39/00* | (2006.01) |

(52) U.S. Cl.

CPC ................ *C12N 15/86* (2013.01); *A61K 39/12* (2013.01); *A61K 39/17* (2013.01); *C07K 14/005* (2013.01); *A61K 2039/5256* (2013.01); *A61K 2039/53* (2013.01); *A61K 2039/54* (2013.01); *A61K 2039/552* (2013.01); *A61K 2039/70* (2013.01); *C12N 2710/16343* (2013.01); *C12N 2720/10034* (2013.01); *C12N 2760/18134* (2013.01)

(58) Field of Classification Search

CPC ........... C12N 2710/16643; C12N 2710/16343; C12N 2760/18122; C12N 2710/10022; C12N 2760/18134; C12N 2710/10034; A61K 39/255; A61K 39/17; A61K 2039/5256; A61K 39/12; A61K 2039/53

See application file for complete search history.

(56) References Cited

U.S. PATENT DOCUMENTS

| | | | | |
|---|---|---|---|---|
| 5,187,087 | A | 2/1993 | Sondermeijer et al. | |
| 5,223,424 | A | 6/1993 | Cochran et al. | |
| 5,250,298 | A | 10/1993 | Gelb, Jr. | |
| 5,273,876 | A | 12/1993 | Hock et al. | |
| 5,279,965 | A | 1/1994 | Keeler, Jr. | |
| 5,310,678 | A | 5/1994 | Bingham et al. | |
| 5,733,554 | A | 3/1998 | Audonnet et al. | |
| 5,830,745 | A | 11/1998 | Hock et al. | |
| 5,834,305 | A | 11/1998 | Cochran et al. | |
| 5,853,733 | A | 12/1998 | Cochran et al. | |
| 5,928,648 | A | 7/1999 | Cochran | |
| 5,961,982 | A | 10/1999 | Cochran | |
| 5,965,138 | A | 10/1999 | Cochran et al. | |
| 5,980,906 | A | 11/1999 | Audonnet et al. | |
| 6,033,670 | A | 3/2000 | Bublot et al. | |
| 6,048,535 | A | 4/2000 | Sharma | |
| 6,121,043 | A | 9/2000 | Cochran et al. | |
| 6,183,753 | B1 | 2/2001 | Cochran et al. | |
| 6,299,882 | B1 | 10/2001 | Junker | |
| 6,322,780 | B1 | 11/2001 | Lee et al. | |
| 6,406,702 | B1 | 6/2002 | Sharma | |
| 6,632,664 | B1 * | 10/2003 | Saitoh et al. | 435/320.1 |
| 6,875,856 | B2 | 4/2005 | Wild et al. | |
| 6,913,751 | B2 | 7/2005 | Cochran et al. | |
| 7,314,715 | B2 | 1/2008 | Cochran et al. | |
| 2002/0081316 | A1 | 6/2002 | Cochran et al. | |
| 2002/0085999 | A1 | 7/2002 | Lee et al. | |
| 2009/0191239 | A1 | 7/2009 | Wild et al. | |
| 2012/0052089 | A1 | 3/2012 | Bublot | |

FOREIGN PATENT DOCUMENTS

| | | | |
|---|---|---|---|
| CA | 2050850 | A1 | 3/1992 |
| EP | 0227414 | B1 | 5/1991 |

(Continued)

OTHER PUBLICATIONS

Afonso, et al., The Genome ofTurkey Herpesvirus, Journal of Virology, 2001, 971-978, 75-2.

(Continued)

*Primary Examiner* — Mary E Mosher

(57) ABSTRACT

The present invention relates to the field of veterinary vaccines, in particular to that of vector vaccines for poultry based on recombinant nonpathogenic Marek's disease virus (npMDV). The recombinant npMDV of the invention expresses stably and effectively two heterologous genes each originating from a different micro-organism: the fusion protein gene from Newcastle disease virus, and the viral protein 2 gene from infectious bursal disease virus. A vaccine based on this recombinant npMDV can be used to induce in poultry a protective immune response not only against Marek's disease, but also against Newcastle disease and Infectious bursal disease. The invention also relates to methods and uses involving the recombinant npMDV, expression cassette, infected host cells, and vaccines.

13 Claims, 5 Drawing Sheets

(56) References Cited

FOREIGN PATENT DOCUMENTS

Figure 1:
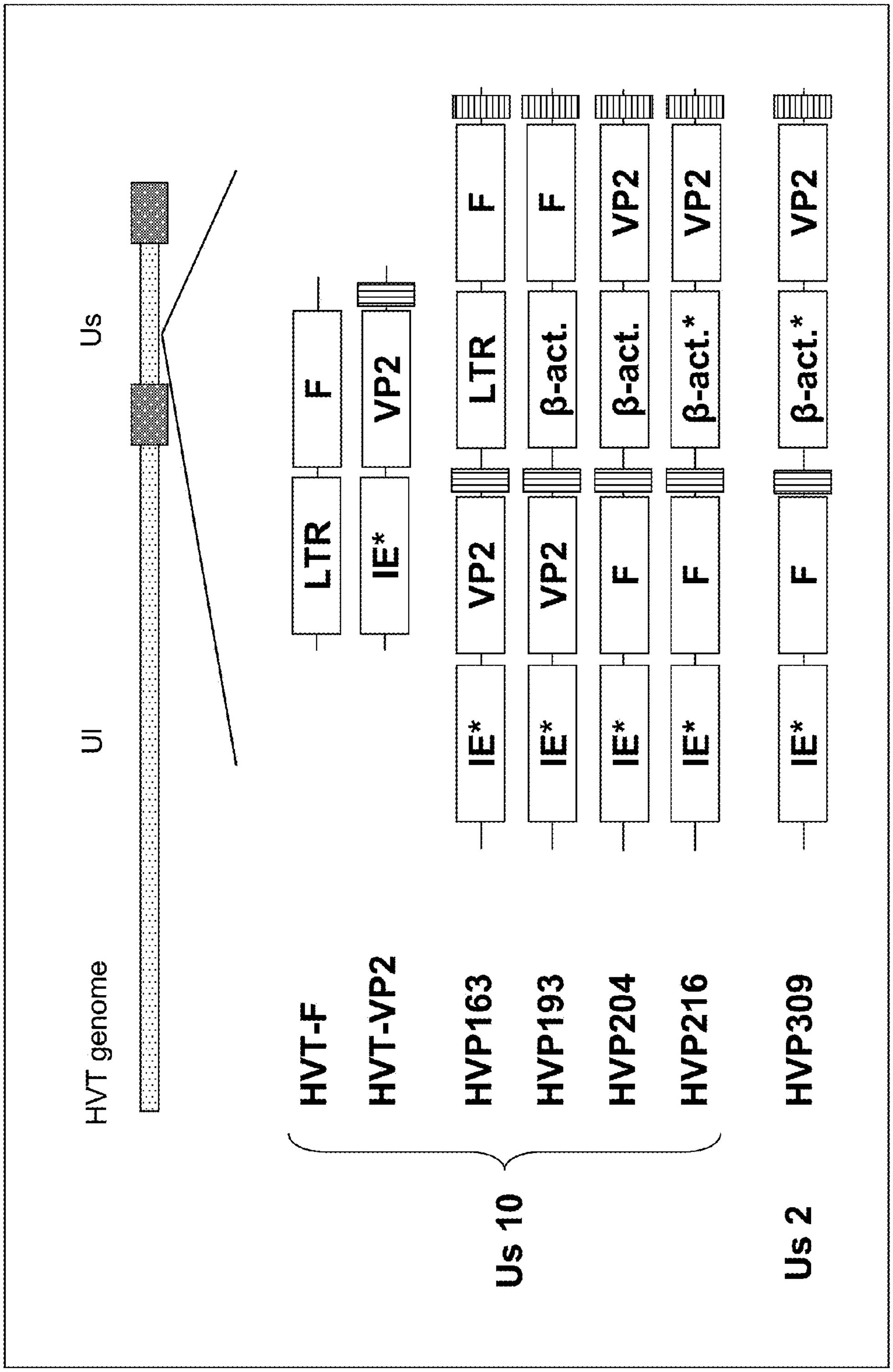

| | | | |
|---|---|---|---|
| EP | 0477056 | A1 | 3/1992 |
| EP | 0332677 | B1 | 7/1995 |
| EP | 1026246 | A1 | 10/2000 |
| EP | 0996464 | B1 | 12/2003 |
| EP | 0794257 | B1 | 10/2006 |
| EP | 1298139 | B1 | 5/2007 |
| EP | 0776361 | B1 | 11/2007 |
| EP | 1801204 | B1 | 2/2011 |
| WO | WO8704663 | A1 | 7/1987 |
| WO | WO9203554 | A1 | 3/1992 |
| WO | WO9325665 | A1 | 12/1993 |
| WO | WO9605291 | A1 | 2/1996 |
| WO | WO9629396 | A1 | 9/1996 |
| WO | WO9837216 | A1 | 11/1996 |
| WO | WO0061736 | A2 | 10/2000 |
| WO | 03075843 | A2 | 9/2003 |
| WO | WO2010125084 | A1 | 11/2010 |

OTHER PUBLICATIONS

Coppo, et al., Immune Responses to Infectious Laryngotracheitis Virus, Dev. Comp. Immunology, 2013, 454-462, 41-3.
Dartiel, et al., Herpesvirus of Turkey Recombinant Viruses Expressing Infectious Bursal Disease Virus (IBDV) VP2 Immunogen Induce Protection Against an IBDV Virulent Challenge in Chickens, Virology, 1995, 481-490, 211.
Fuchs, et al., Molecular Biology of Avian Infectious Laryngotracheitis Virus, Veterinary Research, 2007, 261-279, 38.
Fynan, et al., Persistence of Marek's Disease Virus in a Subpopulation of B Cells that is Transformed by Avian Leukosis Virus, but not in Normal Bursal B Cells, Journal of Virology, 1992, 5860-5866, 66-10.
Gibbs, et al., Extensive Homology Exists Between Marek Disease Herpesvirus and its Vaccine Virus, Herpevsirus of Turkeys, Proceedings of the National Academy of Sciences, USA, 1984, 3365-3369, 81.
Jarosinski, K.W., Dual Infection and Superinfection Inhibition of Epithelial Skin Cells by Two Alphaherpesviruses Co-occur in the Natural Host, PLoS One, 2012, 1-15, 7-5:e37428.
Johnson, et al., Protection Against Infectious Laryngotracheitis by In Ovo Vaccination with Commercially Available Viral Vector Recombinant Vaccines, Avian Diseases, 2010, 1251-1259, 54.
Kingham, et al., The Genome of Herpesvirus of Turkeys: Comparative Analysis with Marek's Disease Viruses, Journal of General Virology, 2001, 1123-1135, 82.
Kulikova, Effects of Infections Bursal Disease Vaccination Straing on the Immune System of Leghorn Chickens, Acta Vet. BRNO, 2004, pp. 205-209, vol. 73.
Lee, et al., The Complete Unique Long Sequence and the Overall Genomic Organization of the GA strain of Marek's Disease Virus, Proceedings of the National Academy of Sciences, USA, 2000, 6091-6096, 97-11.
Martin, et al., Genetic and Biochemical Characterization of the Thymidine Kinase Gene from Herpesvirus of Turkeys, Journal of Virology, 1989, 547-553, 63-6.
Mazariegos, et al., Pathogenicity and Immunosuppressive Properties of Infectious Bursal Disease Intermediate, Avian Diseases, 1990, pp. 203-208, vol. 34.
Morgan, et al., Protection of Chickens from Newcastle and Marek's Diseases with a Recombinant Herpesvirus of Turkeys Vaccine Expressing the Newcastle Disease Virus Fusion Protein, Avian Diseases, 1992, 858-870, 36-4.
Murthy, et al., Pathogenesis of Marek's Disease: Effect of Immunization with Inactivated Viral and Tumor-Associated Antigens, Infection and Immunity, 1979, pp. 547-533, 26-2.
Palya, et al., Advancement in vaccination against Newcastle disease: recombinant HVT NDV provides high clinical protection and reduces challenge virus shedding with the absence of vaccine reactions, Avian Disease, 2012, 282-287, 56-2.
Parsheera, Decisions taken in the 92nd Meeting of the Genetic Engineering Approval Committee, The 92nd Meeting of the Genetically Engineering Approval Committee (GEAC), 2009, 1-5,-.
PCT International Search Report for corresponding PCT/EP2012/07028, mailed on Mar. 13, 2013.
Petherbridge, et al., Cloning of Gallid Herpesvirus 3 (Marek's Disease Virus Serotype-2), Journal of Virological Methods, 2009, 11-17, 158.
Reddy, et al., Protective Efficacy of a Recombinant Herpesvirus of turkeys as an In Ovo Vaccine Against Newcastle and Marek's Diseases in Specific-Pathogen-Free Chickens, Vaccine, 1996, 469-477, 14-6.
Saiki, et al., Primer-Directed Enzymatic Amplification of DNA with a Thermostable DNA Polymerase, Science, 1988, 487-491, 239.
Senne, et al., Control of Newcastle Disease by Vaccination, Dev Biol (Basel), 2004, 165-170, 119.
Sharma, et al., Field Trial in Commercial Broilers with a Multivalent in Ovo Vaccine Comprising a Mixture of Live Viral Vaccines Against Marek's Disease, Infectious Bursal Disease, Newcastle Disease, and Fowl Pox, Avian Diseases, 2002, 613-622, 46-3.
Sondermeijer, et al., Avian Herpesvirus as a Live Viral Vector for the Expression of Heterologous Antigens, Vaccine, 1993, 349-358, 11.
Sun, et al., Protection of Chickens from Newcastle Disease and Infectious Laryngotracheitis with a Recombinant Fowlpox Virus Co-Expressing the F, HN Genes of Newcastle Disease Virus and gB Gene of Infectious Laryngotracheitis Virus, Avian Diseases, 2008, 111-117, 52.
Thompson, et al., Clustal W: Improving the Sensitivity of Progressive Multiple Sequence Alignment through Sequence Weighting, Position-Specific Gap Penalties and Weight Matrix Choice, Nucleic Acids Research, 1994, 4673-5645, 22-22.
Tsukamoto, et al., Complete, Long-Lasting Protection Against Lethal Infectious Bursal Disease Virus Challenge by a Single Vaccination with an Avian Herepesvirus Vector Expressing VP2 Antigens, Journal of Virology, 2002, 5637-5645, 76-11.
Tsukamoto, et al., Protection of Chickens Against Very Virulent Infectious Bursal Disease Virus (IBDV) and Marek's Disease Virus (MDV) with a Recombinant MDV Expressing IBDV VP2, Virology, 1999, 352-362, 257-2.
Vagnozzi, et al., Protection Induced by Commercially Available Live-Attenuated and Recombinant Viral Vector Vaccines Against Infectious Laryngotracheitis Virus in Broiler Chickens, Avian Pathology, 2012, 21-31, 41-1.
Van Zijl, et al., Regeneration of Herpesviruses from Molecularly Cloned Subgenomic Fragments, Journal of Virology, 1988, 2191-2195, 62-6.
Wild, et al., A Genomic map of Infectious Laryngotracheitis Virus and the Sequence and Organization of Genes Present in the Unique Short and Flanking Regions, Virus Genes, 1996, 107-116, 12-2.
Wu, et al., Molecular Detection and Differentiation of Infectious Bursal Disease Virus, Avian Diseases, 2007, 515-526, 51.
International Search Report for PCTEP2012070727.

* cited by examiner

SEQUENCE LISTING

<160> NUMBER OF SEQ ID NOS: 11

<210> SEQ ID NO 1
<211> LENGTH: 361
<212> TYPE: DNA
<213> ORGANISM: Human cytomegalovirus

<400> SEQUENCE: 1

```
cgcgccaggt caattccctg gcattatgcc cagtacatga ccttatggga ctttcctact     60

tggcagtaca tctacgtatt agtcatcgct attaccatgg tgatgcggtt ttggcagtac    120

atcaatgggc gtggatagcg gtttgactca cggggatttc caagtctcca ccccattgac    180

gtcaatggga gtttgttttg gcaccaaaat caacgggact ttccaaaatg tcgtaacaac    240

tccgccccat tgacgcaaat gggcggtagg cgtgtacggt gggaggtcta tataagcaga    300

gctcgtttag tgaaccgtca gatcgcctgg agacgccatc cacgctgttt tgacctccat    360

a                                                                    361
```

<210> SEQ ID NO 2
<211> LENGTH: 1662
<212> TYPE: DNA
<213> ORGANISM: Newcastle disease virus

<400> SEQUENCE: 2

```
atgggcccca gaccttctac caagaaccca gtacctatga tgctgactgt ccgagtcgcg     60

ctggtactga gttgcatctg tccggcaaac tccattgatg gcaggcctct tgcggctgca    120

ggaattgtgg ttacaggaga caaagccgtc aacatataca cctcatccca gacaggatca    180

atcatagtta agctcctccc gaatctgccc aaggataagg aggcatgtgc gaaagccccc    240

ttggatgcat acaacaggac attgaccact ttgctcaccc cccttggtga ctctatccgt    300

aggatacaag agtctgtgac tacatctgga ggggggagac aggggcgcct tataggcgcc    360

attattggcg gtgtggctct tggggttgca actgccgcac aaataacagc ggccgcagct    420

ctgatacaag ccaaacaaaa tgctgccaac atcctccgac ttaaagagag cattgccgca    480

accaatgagg ctgtgcatga ggtcactgac ggattatcgc aactagcagt ggcagttggg    540

aagatgcagc agtttgttaa tgaccaattt aataaaacag ctcaggaatt agactgcatc    600

aaaattgcac agcaagttgg tgtagagctc aacctgtacc taaccgaatt gactacagta    660

ttcggaccac aaatcacttc acctgcttta aacaagctga ctattcaggc actttacaat    720

ctagctggtg gaaatatgga ttacttattg actaagttag gtgtagggaa caatcaactc    780

agctcattaa tcggtagcgg cttaatcacc ggtaacccta ttctatacga ctcacagact    840

caactcttgg gtatacaggt aactctacct tcagtcggga acctaaataa tatgcgtgcc    900

acctacttgg aaaccttatc cgtaagcaca accaggggat ttgcctcggc acttgtccca    960

aaagtggtga cacaggtcgg ttctgtgata gaagaacttg acacctcata ctgtatagaa   1020

actgacttag atttatattg tacaagaata gtaacgttcc ctatgtcccc tggtatttat   1080

tcctgcttga gcggcaatac gtcggcctgt atgtactcaa agaccgaagg cgcacttact   1140

acaccataca tgactatcaa aggttcagtc atcgccaact gcaagatgac aacatgtaga   1200
```

```
tgtgtaaacc ccccgggtat catatcgcaa aactatggag aagccgtgtc tctaatagat   1260

aaacaatcat gcaatgtttt atccttaggc gggataactt taaggctcag tggggaattc   1320

gatgtaactt atcagaagaa tatctcaata caagattctc aagtaataat aacaggcaat   1380

cttgatatct caactgagct tgggaatgtc aacaactcga tcagtaatgc tttgaataag   1440

ttagaggaaa gcaacagaaa actagacaaa gtcaatgtca aactgactag cacatctgct   1500

ctcattacct atatcgtttt gactatcata tctcttgttt ttggtatact tagcccgatt   1560

ctagcatgct acctaatgta caagcaaaag gcgcaacaaa agaccttatt atggcttggg   1620

aataatactc tagatcagat gagagccact acaaaaatgt ga                      1662


<210> SEQ ID NO 3
<211> LENGTH: 281
<212> TYPE: DNA
<213> ORGANISM: Human cytomegalovirus

<400> SEQUENCE: 3

ggaattctag atcccacgtc actattgtat actctatatt atactctatg ttatactctg     60

taatcctact caataaacgt gtcacgcctg tgaaaccgta ctaagtctcc cgtgtcttct    120

tatcaccatc aggtgacatc ctcgcccagg ctgtcaatca tgccggtatc gattccagta    180

gcaccggccc cacgctgaca acccactctt gcagcgttag cagcgcccct cttaacaagc    240

cgaccccccac cagcgtcgcg gttactaaca ctcctctccc c                       281


<210> SEQ ID NO 4
<211> LENGTH: 696
<212> TYPE: DNA
<213> ORGANISM: Gallus gallus

<400> SEQUENCE: 4

ctagtggcgc gccggatcag atctccatgg gtcgaggtga gccccacgtt ctgcttcact     60

ctccccatct cccccccctc cccaccccca attttgtatt tatttatttt ttaattattt    120

tgtgcagcga tgggggcggg gggggggggg gcgcgcgcca ggcggggcgg ggcggggcga    180

ggggcggggc ggggcgaggc ggagaggtgc ggcggcagcc aatcagagcg gcgcgctccg    240

aaagtttcct tttatggcga ggcggcggcg gcggcggccc tataaaaagc gaagcgcgcg    300

gcgggcggga gtcgctgcgt tgccttcgcc ccgtgccccg ctccgcgccg cctcgcgccg    360

cccgccccgg ctctgactga ccgcgttact cccacaggtg agcgggcggg acggcccttc    420

tcctccgggc tgtaattagc ggcaggaagg aaatgggcgg ggagggcctt cgtgcgtcgc    480

cgcgccgccg tccccttctc catctccagc ctcggggctg ccgcaggggg acggctgcct    540

tcgggggggga cggggcaggg cggggttcgg cttctggcgt gtgaccggcg gctctagagc    600

ctctgctaac catgttcatg ccttcttctt tttcctacag ctcctgggca acgtgctggt    660

tgttgtgctg tctcatcatt ttggcaaaga attgca                              696


<210> SEQ ID NO 5
<211> LENGTH: 1362
<212> TYPE: DNA
<213> ORGANISM: Infectious bursal disease virus

<400> SEQUENCE: 5

atgacaaacc tgcaagatca aacccaacag attgttccgt tcatacggag ccttctgatg     60

ccaacaaccg gaccggcgtc cattccggac gacaccctgg agaagcacac tctcaggtca    120
```

-continued

```
gagacctcga cctacaattt gactgtgggg gacacagggt cagggctaat tgtctttttc    180

cctggattcc ctggctcaat tgtgggtgct cactacacac tgcagagcaa tgggaactac    240

aagttcgatc agatgctcct gactgcccag aacctaccgg ccagctacaa ctactgcaga    300

ctagtgagtc ggagtctcac agtgaggtca agcacactcc ctggtggcgt ttatgcacta    360

aacggcacca taaacgccgt gaccttccaa ggaagcctga gtgaactgac agatgttagc    420

tacaatgggt tgatgtctgc aacagccaac atcaacgaca aagttgggaa tgtcctggta    480

ggggaagggg tcactgtcct cagcctaccc acatcatatg atcttgggta tgtgaggctt    540

ggtgacccca ttcccgctat agggcttgac ccaaaaatgg tagctacatg cgacagcagt    600

gacaggccca gagtctacac cataactgca gccgatgatt accaattctc atcacagtac    660

caaccaggtg gggtaacaat cacactgttc tcagccaaca ttgatgctat cacaagcctc    720

agcattgggg gagagctcgt gtttcaaaca agcgtccaag gccttgtact gggcgccacc    780

atctacctta taggctttga tgggactgcg gtaatcacca gagctgtggc cgcagataat    840

gggctgacgg ccggcaccga caatcttatg ccattcaatc ttgtcattcc aaccaatgag    900

ataacccagc cgatcacatc catcaaactg gagatagtga cctccaaaag tggtggtcag    960

gcaggggatc agatgtcatg gtcggcaagt gggagcctag cagtgacgat ccatggtggc   1020

aactatccag ggccctccg tcccgtcaca ctagtagcct acgaaagagt ggcaacagga   1080

tccgtcgtta cggtcgctgg ggtgagtaac ttcgagctga tcccaaatcc tgaactagca   1140

aagaacctgg ttacagaata cggccgattt gacccaggag ccatgaacta cacaaaattg   1200

atactgagtg agagggaccg tcttggcatc aagaccgtct ggccaacaag ggagtacact   1260

gattttcgtg agtacttcat ggaggtggcc gacctcaact ctcccctgaa gattgcagga   1320

gcatttggct tcaaagacat aatccgggct ataaggaggt aa                      1362


<210> SEQ ID NO 6
<211> LENGTH: 55
<212> TYPE: DNA
<213> ORGANISM: Feline herpesvirus 1

<400> SEQUENCE: 6

caataaacat agcatacgtt atgacatggt ctaccgcgtc ttatatgggg acgac          55


<210> SEQ ID NO 7
<211> LENGTH: 4525
<212> TYPE: DNA
<213> ORGANISM: Artificial Sequence
<220> FEATURE:
<223> OTHER INFORMATION: Expression cassette insert of recombinant HVT
      construct HVP-309
<220> FEATURE:
<221> NAME/KEY: promoter
<222> LOCATION: (30)..(390)
<223> OTHER INFORMATION: hCMV-IE1 gene core promoter
<220> FEATURE:
<221> NAME/KEY: misc_feature
<222> LOCATION: (415)..(2076)
<223> OTHER INFORMATION: Fusion protein gene from NDV Clone 30
<220> FEATURE:
<221> NAME/KEY: terminator
<222> LOCATION: (2088)..(2368)
<223> OTHER INFORMATION: hCMV-IE1 gene transcription terminator
<220> FEATURE:
<221> NAME/KEY: promoter
<222> LOCATION: (2378)..(3073)
<223> OTHER INFORMATION: Chicken beta-actin gene core promoter
<220> FEATURE:
<221> NAME/KEY: misc_feature
<222> LOCATION: (3085)..(4446)
```

-continued

<223> OTHER INFORMATION: VP2 gene from IBDV Faragher 52/70
<220> FEATURE:
<221> NAME/KEY: terminator
<222> LOCATION: (4470)..(4524)
<223> OTHER INFORMATION: FHV1-Us transcription terminator

<400> SEQUENCE: 7

```
agcttaatta agtaccgagc tcgaattggc gcgccaggtc aattccctgg cattatgccc     60
agtacatgac cttatgggac tttcctactt ggcagtacat ctacgtatta gtcatcgcta    120
ttaccatggt gatgcggttt tggcagtaca tcaatgggcg tggatagcgg tttgactcac    180
ggggatttcc aagtctccac cccattgacg tcaatgggag tttgttttgg caccaaaatc    240
aacgggactt tccaaaatgt cgtaacaact ccgccccatt gacgcaaatg ggcggtaggc    300
gtgtacggtg ggaggtctat ataagcagag ctcgtttagt gaaccgtcag atcgcctgga    360
gacgccatcc acgctgtttt gacctccata gaagacaccg ggcgcgccgg atccatgggc    420
cccagacctt ctaccaagaa cccagtacct atgatgctga ctgtccgagt cgcgctggta    480
ctgagttgca tctgtccggc aaactccatt gatggcaggc ctcttgcggc tgcaggaatt    540
gtggttacag gagacaaagc cgtcaacata tacacctcat cccagacagg atcaatcata    600
gttaagctcc tcccgaatct gcccaaggat aaggaggcat gtgcgaaagc cccccttggat   660
gcatacaaca ggacattgac cactttgctc acccccccttg gtgactctat ccgtaggata   720
caagagtctg tgactacatc tggagggggg agacaggggc gccttatagg cgccattatt    780
ggcggtgtgg ctcttggggt tgcaactgcc gcacaaataa cagcggccgc agctctgata    840
caagccaaac aaaatgctgc caacatcctc cgacttaaag agagcattgc cgcaaccaat    900
gaggctgtgc atgaggtcac tgacggatta tcgcaactag cagtggcagt tgggaagatg    960
cagcagtttg ttaatgacca atttaataaa acagctcagg aattagactg catcaaaatt   1020
gcacagcaag ttggtgtaga gctcaacctg tacctaaccg aattgactac agtattcgga   1080
ccacaaatca cttcacctgc tttaaacaag ctgactattc aggcacttta caatctagct   1140
ggtggaaata tggattactt attgactaag ttaggtgtag ggaacaatca actcagctca   1200
ttaatcggta gcggcttaat caccggtaac cctattctat acgactcaca gactcaactc   1260
ttgggtatac aggtaactct accttcagtc gggaacctaa ataatatgcg tgccacctac   1320
ttggaaacct tatccgtaag cacaaccagg ggatttgcct cggcacttgt cccaaaagtg   1380
gtgacacagg tcggttctgt gatagaagaa cttgacacct catactgtat agaaactgac   1440
ttagatttat attgtacaag aatagtaacg ttccctatgt cccctggtat ttattcctgc   1500
ttgagcggca atacgtcggc ctgtatgtac tcaaagaccg aaggcgcact tactacacca   1560
tacatgacta tcaaaggttc agtcatcgcc aactgcaaga tgacaacatg tagatgtgta   1620
aaccccccgg gtatcatatc gcaaaactat ggagaagccg tgtctctaat agataaacaa   1680
tcatgcaatg ttttatcctt aggcgggata actttaaggc tcagtgggga attcgatgta   1740
acttatcaga agaatatctc aatacaagat tctcaagtaa taataacagg caatcttgat   1800
atctcaactg agcttgggaa tgtcaacaac tcgatcagta atgctttgaa taagttagag   1860
gaaagcaaca gaaaactaga caaagtcaat gtcaaactga ctagcacatc tgctctcatt   1920
acctatatcg ttttgactat catatctctt gtttttggta tacttagccc gattctagca   1980
tgctacctaa tgtacaagca aaaggcgcaa caaaagacct tattatggct tgggaataat   2040
actctagatc agatgagagc cactacaaaa atgtgaggat ctctcgagga attctagatc   2100
ccacgtcact attgtatact ctatattata ctctatgtta tactctgtaa tcctactcaa   2160
```

-continued

```
taaacgtgtc acgcctgtga aaccgtacta agtctcccgt gtcttcttat caccatcagg   2220
tgacatcctc gcccaggctg tcaatcatgc cggtatcgat tccagtagca ccggccccac   2280
gctgacaacc cactcttgca gcgttagcag cgcccctctt aacaagccga cccccaccag   2340
cgtcgcggtt actaacactc ctctccccga cctgcaacta gtggcgcgcc ggatcagatc   2400
tccatgggtc gaggtgagcc ccacgttctg cttcactctc cccatctccc ccccctcccc   2460
acccccaatt ttgtatttat ttatttttta attattttgt gcagcgatgg gggcgggggg   2520
gggggggcg cgcgccaggc ggggcggggc ggggcgaggg gcggggcggg gcgaggcgga   2580
gaggtgcggc ggcagccaat cagagcggcg cgctccgaaa gtttcctttt atggcgaggc   2640
ggcggcggcg gcggccctat aaaaagcgaa gcgcgcggcg ggcgggagtc gctgcgttgc   2700
cttcgccccg tgccccgctc cgcgccgcct cgcgccgccc gccccggctc tgactgaccg   2760
cgttactccc acaggtgagc gggcgggacg gcccttctcc tccgggctgt aattagcggc   2820
aggaaggaaa tgggcgggga gggccttcgt gcgtcgccgc gccgccgtcc ccttctccat   2880
ctccagcctc ggggctgccg caggggggacg gctgccttcg ggggggacgg ggcagggcgg   2940
ggttcggctt ctggcgtgtg accggcggct ctagagcctc tgctaaccat gttcatgcct   3000
tcttcttttt cctacagctc ctgggcaacg tgctggttgt tgtgctgtct catcattttg   3060
gcaaagaatt gcagatctgg atctatgaca aacctgcaag atcaaaccca acagattgtt   3120
ccgttcatac ggagccttct gatgccaaca accggaccgg cgtccattcc ggacgacacc   3180
ctggagaagc acactctcag gtcagagacc tcgacctaca atttgactgt gggggacaca   3240
gggtcagggc taattgtctt tttccctgga ttccctggct caattgtggg tgctcactac   3300
acactgcaga gcaatgggaa ctacaagttc gatcagatgc tcctgactgc ccagaaccta   3360
ccggccagct acaactactg cagactagtg agtcggagtc tcacagtgag gtcaagcaca   3420
ctccctggtg gcgtttatgc actaaacggc accataaacg ccgtgacctt ccaaggaagc   3480
ctgagtgaac tgacagatgt tagctacaat gggttgatgt ctgcaacagc caacatcaac   3540
gacaaagttg ggaatgtcct ggtaggggaa ggggtcactg tcctcagcct acccacatca   3600
tatgatcttg ggtatgtgag gcttggtgac cccattcccg ctatagggct tgacccaaaa   3660
atggtagcta catgcgacag cagtgacagg cccagagtct acaccataac tgcagccgat   3720
gattaccaat tctcatcaca gtaccaacca ggtggggtaa caatcacact gttctcagcc   3780
aacattgatg ctatcacaag cctcagcatt gggggagagc tcgtgtttca aacaagcgtc   3840
caaggccttg tactgggcgc caccatctac cttataggct ttgatgggac tgcggtaatc   3900
accagagctg tggccgcaga taatgggctg acggccggca ccgacaatct tatgccattc   3960
aatcttgtca ttccaaccaa tgagataacc cagccgatca catccatcaa actggagata   4020
gtgacctcca aaagtggtgg tcaggcaggg gatcagatgt catggtcggc aagtgggagc   4080
ctagcagtga cgatccatgg tggcaactat ccaggggccc tccgtcccgt cacactagta   4140
gcctacgaaa gagtggcaac aggatccgtc gttacggtcg ctggggtgag taacttcgag   4200
ctgatcccaa atcctgaact agcaaagaac ctggttacag aatacggccg atttgaccca   4260
ggagccatga actacacaaa attgatactg agtgagaggg accgtcttgg catcaagacc   4320
gtctggccaa caagggagta cactgatttt cgtgagtact tcatggaggt ggccgacctc   4380
aactctcccc tgaagattgc aggagcattt ggcttcaaag acataatccg ggctataagg   4440
aggtaagatc cgatctctcg attaattaac aataaacata gcatacgtta tgacatggtc   4500
```

-continued taccgcgtct tatatgggga cgaca 4525

<210> SEQ ID NO 8
<211> LENGTH: 20
<212> TYPE: DNA
<213> ORGANISM: Artificial Sequence
<220> FEATURE:
<223> OTHER INFORMATION: PCR/sequencing primer

<400> SEQUENCE: 8
tcacactagt tgggtttatc 20

<210> SEQ ID NO 9
<211> LENGTH: 22
<212> TYPE: DNA
<213> ORGANISM: Artificial Sequence
<220> FEATURE:
<223> OTHER INFORMATION: PCR/sequencing primer

<400> SEQUENCE: 9
acgtagatgt actgccaagt ag 22

<210> SEQ ID NO 10
<211> LENGTH: 20
<212> TYPE: DNA
<213> ORGANISM: Artificial Sequence
<220> FEATURE:
<223> OTHER INFORMATION: PCR/sequencing primer

<400> SEQUENCE: 10
ccgggctata aggaggtaag 20

<210> SEQ ID NO 11
<211> LENGTH: 20
<212> TYPE: DNA
<213> ORGANISM: Artificial Sequence
<220> FEATURE:
<223> OTHER INFORMATION: PCR/sequencing primer

<400> SEQUENCE: 11
gtacgcgtcc gggtatacac 20

RECOMBINANT NONPATHOGENIC MDV VECTOR PROVIDING MULTIVALENT IMMUNITY

CROSS-REFERENCE TO RELATED APPLICATIONS

This application is a national stage entry under 35 U.S.C. §371 of PCT/EP2012/070727, filed on Oct. 19, 2012, which claims priority to EP Application No. 11186237.1, filed on Oct. 21, 2011. The content of PCT/EP2012/070727 is hereby incorporated by reference in its entirety.

The present invention relates to the field of veterinary vaccines, in particular to that of viral vector vaccines for poultry, based on recombinant nonpathogenic Marek's disease viruses.

Marek's disease viruses (MDV) form a family of alphaherpesvirideae infecting avian species. The virion is enveloped, and about 160 nm in size. Within the capsid they comprise a large genome of linear double stranded DNA.

MDV serotype 1 (MDV1), also named Gallid herpesvirus 2, is pathogenic to chickens and occurs worldwide. It is tumorogenic and causes lymphomas and paralysis. Attenuated MDV1 strains have been used as vaccine, e.g. the Rispens vaccine (strain CVI-988) (Kreager, 1998, Poultry Sci., vol. 77, p. 1213)

MDV serotype 2 (MDV2), also known as Gallid herpesvirus 3, is a strongly attenuated to practically apathogenic MDV of chickens (Petherbridge et al., 2009, J. Virol. Meth., vol. 158, p. 11), which is commonly used as vaccine against MDV1. A well known vaccine of MDV2 is Nobilis™ Marexine SB1 (MSD Animal Health).

MDV serotype 3 is also known as: Meleagrid herpesvirus 1, turkey herpesvirus, but most commonly as: herpes virus of turkeys (HVT). This was described around 1970 as a herpesvirus infecting turkeys (Witter et al, 1970, Am. J. Vet. Res., vol. 31, p. 525), which was apathogenic to chickens. Strains of HVT such as PB1 or FC-126 are commonly used to vaccinate against MDV1. Alternatively, when protection against very virulent MDV1 is required, HVT is used in combination with an MDV2 vaccine-strain, e.g. with SB1 in Nobilis™ Marexine CA126+SB1 (MSD Animal Health), or with an MDV1 vaccine strain such as Rispens in Nobilis™ RISMAVAC+CA126 (MSD Animal Health).

The nonpathogenic Marek's disease viruses (npMDV) MDV2 and HVT replicate in the birds' peripheral blood lymphocytes (PBL's), consequently they are systemic viruses, which induce an immune response of long duration, which is mostly aimed at the cellular-, and not at the humoral immune system.

npMDV vaccines can be applied to chickens at an early age, which is a combined result of their safe apathogenic nature, as well as a relative insensitivity to maternally derived antibodies (MDA) against MDV2 or HVT; MDA in chicks are antibodies derived via the egg from their mothers, who as a routine are vaccinated thoroughly against common poultry pathogens. Consequently, npMDV vaccines can be inoculated into chicks as early as the day of their hatching from the egg (day one), or even before hatching, while still in the egg. This last approach, so-called 'in ovo vaccination', is a form of embryo vaccination, which is commonly applied at day 18 of embryonic development (ED), about 3 days before hatch.

The heterologous gene that is expressed in a live recombinant vector is typically encoding a protein (or the relevant part thereof) that is the major host-protective immunogen of the micro-organism that is to be vaccinated against; as this protein or peptide carries the immunodominant epitope(s), of such a micro-organism, it can induce the host's immune system to produce neutralising antibodies and/or a cellular immunity that will clear the micro-organism from a vaccinated target animal.

Next to being used as a vaccine per se, HVT is also being used as a viral vector vaccine for the expression and delivery of various immunogenic proteins to a poultry animal, see WO 87/04463. Several genes coding for antigens from poultry pathogens have been expressed in HVT vectors, such as from: Newcastle disease virus (NDV) (Sondermeijer et al., 1993, Vaccine, vol. 11, p. 349-358), and infectious bursal disease virus (IBDV) (Darteil et al., 1995, Virology, vol. 211, p. 481-490). But also the expression has been described of a parasite antigen (Cronenberg et al., 1999, Acta Virol., vol. 43, p. 192-197), and of a cytokine, to manipulate the chicken's immune response (WO 2009/156.367; Tarpey et al., 2007, Vaccine, vol. 25, p. 8529-8535).

The administration of an HVT vector vaccine to poultry generates an immune response against the expressed heterologous gene, as well as against HVT which protects against MDV. This is applied in a variety of commercial HVT vector vaccine products, for instance: the NDV F protein gene: Innovax™-ND (MSD Animal Health), and Vectormune™ HVT-NDV (Ceva); or the IBDV VP2 gene: Vaxxitek™ HVT+IBD (Merial; previously named: Gallivac™ HVT–IBD), and Vectormune™ HVT–IBD (Ceva);

The genomic nucleotide sequence of HVT is available, for example from Genbank™ as: AF291866 (strain FC-126). Several methods have been described for inserting heterologous nucleic acids into HVT, such as by using homologous recombination (Sondermeijer et al., supra), cosmid regeneration (U.S. Pat. No. 5,961,982), or Bacmids (bacterial artificial chromosomes) (Baigent et al., 2006, J. of Gen. Virol., vol. 87, p. 769-776).

Many genetic locations for the insertion of a heterologous gene-construct into the HVT genome have been investigated, and several suitable, non-essential, loci have been described, e.g. in the unique short region of the HVT genome (EP 431.668); or in the HVT unique long region (EP 794.257).

Different promoters have been used to drive the expression of the heterologous gene in expression cassettes for HVT, such as: the PRV gpX promoter (WO 87/04.463); the Rous sarcoma virus LTR promoter, the SV40 early gene promoter, and the human cytomegalovirus immediate early1 (hCMV IE1) gene promoter (EP 719.864); or the chicken beta-actin gene promoter (EP 1.298.139).

Similarly, the genomic nucleotide sequences of MDV2 strains are available from Genbank™: HQ840738 (SB1), and AB049735 (HPRS24). The genome organization of MDV2 is very similar to that of HVT, with the Us region in particular, being identical to that of HVT (Kingham et al., 2001, J. of Gen. Virol., vol. 82, p. 1123; Spatz & Schat, 2011, Virus genes, vol. 42, p. 331). Cloning and transfection of MDV2 virus has been described (Petherbridge et al., supra).

For the construction of recombinant vectors, the heterologous construct that is to be inserted into the vector's genome is usually a nucleic acid molecule comprising at least one (heterologous) gene or coding region, which must be capable of encoding (at least an immunogenic part of) an antigenic protein. Also the construct may comprise a promoter sequence to drive the expression of the heterologous gene. In this last case the construct is often termed an 'expression cassette'.

The resulting effect of the insertion of an expression cassette into a vector's genome may differ, as this genome may become larger, the same, or smaller in size, depending from whether the net result on the genome is an addition, replacement or deletion of genetic material, respectively. Also the location of the insertion may vary: placed inside a coding or in a non-coding region of the genome; and the placing may be within or in-between the vector's genes or regulatory areas. These choices determine what the ultimate composition of the expression cassette must be, and what will be its effect on the vector and ultimately on the vaccinated target animal.

Whatever the precise construct, a favourable expression cassette must allow the live recombinant viral vector to overcome a number of biological stresses upon its stability and efficacy: first, the capability to generate progeny after having received the heterologous insert. This indicates the recombinant virus is viable, in spite of the insertion into its genome. Next, the capability to replicate in vitro in a host cell-line for many cycles while maintaining the replication and expression of the heterologous insert. This indicates the recombinant was not attenuated in its replication by the insertion, and the insert is stably maintained and expressed. Thirdly, replication and expression in vivo. This indicates the recombinant virus can overcome the strong selection pressure in a live animal, such as posed by its immune system. In this environment the loss of expression of the foreign gene favours a faster replication in the animal; such 'escape mutants' have acquired mutations or major deletions in the foreign gene or its regulatory region, and could overgrow the intact virus vectors. Finally, and most importantly, the vector replication and the heterologous gene's expression in the animal needs to be able to generate such an effective immune response that the inoculated animal is protected against infection and/or disease, that would otherwise be caused by the micro-organism that was the donor of the heterologous insert that the vector expresses.

Consequently, the resulting recombinant vector must provide a stable integration of the expression cassette in its genome; a good replication of the resulting recombinant vector, both in vitro and in vivo; and an effective expression of the heterologous gene(s) in vivo, preferably of high level, and consistent over time, to induce and maintain a protective immune-response.

This combination of features will allow for the extensive rounds of replication in vitro that are necessary for large scale production, as well as for the continued expression and presentation to the host's immune system of the inserted foreign gene, when the vector vaccine is replicating in an inoculated target animal. In addition, this stability in replication and in expression is required of the vector vaccine to comply with the very high standards of safety and biological stability that must be met by a recombinant virus that is to be introduced into the field as a commercial product after obtaining a marketing authorisation from national governmental authorities.

Newcastle disease and infectious bursal disease are important diseases of poultry, which occur worldwide, and can cause severe negative effects in the poultry industry, regarding animal welfare and economy of operation (see: Disease of poultry, $12^{th}$ ed., 2008, Y. Saif ed., Iowa State Univ. press, ISBN-10: 0813807182).

Newcastle disease viruses belong to the order of the Mononegavirales, specifically of the family of Paramyxoviridae, and can be grouped into distinct pathotypes according to their virulence; the non-pathogenic lentogenic type NDV's hardly cause symptoms in poultry. In contrast, the mesogenic (medium pathogenic) and velogenic (highly pathogenic) NDV strains cause extensive disease and mortality, and are therefore notifiable diseases in many countries. Disease symptoms include respiratory and nervous abnormalities, with gasping and 'torticollis' as most notable.

In commercial poultry operations, protection against infection and/or disease caused by pathogenic NDV strains is achieved by routine vaccination of poultry, typically at day of hatch, with live lentogenic NDV strains, such as Nobilis™ ND Clone 30 (MSD Animal Health).

NDV has a non-segmented, negative sense, single stranded RNA genome, which is about 15 kb in length, and contains six genes, amongst which is the gene for the F glycoprotein, the immunodominant protein. The F protein is involved in NDV's attachment of- and entry into host cells, and can be the basis of an effective immune response against NDV. It is expressed as a native F0 protein, which is cleaved extracellularly into F1 and F2 by peptidases. The ease of cleavage is determined by the amino acid sequence of certain basic amino acids located at the F1/F2 cleavage site, and this determines the virulence of NDV strains.

Infectious bursal disease virus (IBDV), also called Gumboro disease virus, is the causative agent of infectious bursal disease, and is a member of the Birnaviridae family. The viruses in this family have a genome consisting of two segments (A and B) of double-stranded RNA. The larger segment A encodes a polyprotein of 110 kDa, which is subsequently cleaved by autoproteolysis to form mature viral proteins VP2, VP3 and VP4. Of these, VP2 and VP3 are the structural capsid proteins for the virion, and VP2 is the major host-protective immunogen.

In the case of IBDV, two serotypes exist, serotype 1 and 2. The two serotypes can be differentiated by virus neutralisation (VN) tests. Serotype 1 viruses have been shown to be pathogenic to chickens, while serotype 2 IBDV only causes sub-acute disease in turkeys.

Historically, IBDV serotype 1 viruses consisted of only one type that is known as "classic" IBD virus. Recently, so-called "variant" IBDV strains emerged; classic and variant strains can be identified and distinguished by a virus neutralisation test using a panel of monoclonal antibodies or by RT-PCR; this is reviewed by Wu et al. (2007, Avian Diseases, vol. 51, p. 515-526). Well known classic IBDV strains are: D78, Faragher 52/70, and STC.

IBDV is an acute, highly-contagious viral infection of a chicken's lymphoid tissue, with as its primary target the bird's essential immunological organ: the bursa of Fabricius. The morbidity rate in susceptible flocks is high, with rapid weight loss and moderate to high mortality rates. Chicks that recover from the disease may have immune deficiencies because of destruction of (parts of) the bursa of Fabricius. This makes them vulnerable to secondary infections.

In the field, virulence of the circulating wild type IBDV appears to be gradually increasing from virulent to very virulent strains. This may require adaptation of the vaccines used.

Routine vaccinations against IBD are performed as early as possible in the life of a chick using live IBDV strains, but these can only be applied when the level of MDA against IBDV has decreased enough, which commonly is somewhere between 7 and 30 days post hatch, typically between day 15-20. Many live or inactivated IBDV vaccines are commercially available, e.g. a live vaccine such as Nobilis™ Gumboro D78 (MSD Animal Health).

To achieve cost efficiency, a common approach is to design vaccines that comprise combinations of antigens. In this way a single vaccination round can immunise the birds against a number of diseases at once. Not only does this save time and labour costs, but it also reduces discomfort and stress to the vaccinated animals that would otherwise occur from having to receive repeated vaccinations. The highest efficiency in this regard is achieved in the case of vaccinations that are not given by mass application such as by spray or via drinking water, but that need to be applied individually by injection. An example of this is the vaccination of layer and breeder chickens with an inactivated subunit vaccine. These have now been developed into combination vaccines comprising up to 7 different antigens; e.g. Nobilis™ Cor4+IB+ND+EDS (MSD Animal health).

Because vaccines based on recombinant npMDV as viral vector also need to be administered by individual injection, therefore combinations in this context are also highly desirable. An ability to protect against several different diseases (in addition to MDV protection from the NPMDV vector itself) at once, would be a great benefit. Therefore many groups have investigated the combined expression and delivery of more than one heterologous antigen by npMDV vector vaccination.

An obvious approach was to combine existing recombinant npMDV vector vaccines, each containing a single heterologous insert. However, it has been found in the past that this does not work out well, therefore the product information for existing HVT recombinant vaccines recommends against their combination with other (single) HVT recombinants.

Probably because of competitive selection in the inoculated target animal, one of the recombinant npMDV strains was able to overgrow the other. As a result, only one recombinant vaccine strain was able to replicate efficiently and thus produce immune protection against only one of the relevant pathogens.

The alternative was to construct an npMDV vector that carried multiple heterologous inserts in one recombinant genome. This has been studied already since the first recombinant npMDV constructs were developed (WO 87/044630), and several multivalent insert combinations in HVT have indeed been described over time, for example: in WO 93/25665, the "bivalent vaccines" of Example 11, constructs HVT-007, HVT-048, and HVT-096; similarly, in WO 96/05291, the "bivalent vaccines" of examples 11-14, and even "trivalent vaccines" of examples 16-17. The same applies to the HVT recombinants as described in EP 719.864.

While most of these constructs are only suggested, some of the described vectors with multiple inserts were actually isolated; some were even tested in SPF (specific pathogen free) chickens. However, for most of these multivalent expression constructs, no results were ever published of any studies into the genetic stability of these constructs, or into the expression of the heterologous inserts over time, neither in vitro nor in vivo.

In fact, from the many prior art publications, the only recombinant npMDV with multiple inserts that has been thoroughly tested and was proven to be safe, stable, and effective as a vaccine, is the construct comprising the gD and gI genes from infectious laryngotracheitis virus (ILTV), which is commercially available as Innovax™-ILT (MSD Animal Health).

However, even in this case the heterologous inserts still only provide a monovalent protection against a single poultry pathogen, namely ILTV. This is because the ILTV gD/gI genes naturally overlap and need to be expressed in combination to allow proper immunisation against ILTV. Therefore the multiple insertion was out of a necessity, not an intention to broaden the scope of the immunisation.

Consequently, until today, and in spite of great potential advantages and many attempts over time, there is no prior art describing a safe, stable, and effective recombinant npMDV vector vaccine that provides for the expression of more than one heterologous gene which each originate from a different micro-organism, and thereby allow for the generation of a multivalent immune response (in addition to that against MDV) by the inoculation with a single recombinant npMDV vector vaccine.

It is an object of the present invention to accommodate to this need in the field, and to provide, for the first time, a safe and stable recombinant npMDV vector vaccine, that allows the effective immunisation of poultry against more than one poultry pathogen (in addition to the protection against MDV).

It was surprisingly found that this objective was met by the recombinant npMDV according to the invention, which provides the expression of heterologous immunoprotective antigens from more than one poultry pathogen.

Therefore the invention relates to a recombinant nonpathogenic Marek's disease virus (npMDV) comprising a heterologous nucleic acid molecule, characterised in that said heterologous nucleic acid molecule comprises in 5' to 3' direction, and in this order:

a. a human cytomegalovirus immediate early 1 gene (hCMV-IE1) core promoter, b. a Newcastle disease virus (NDV) fusion (F) protein gene, c. a transcription terminator, d. a chicken beta-actin gene core promoter, e. a classic type infectious bursal disease virus (IBDV) viral protein 2 (VP2) gene, This was not at all straightforward as the inventors found in the course of their experiments, because many recombinant npMDVs described in the prior art for bivalent or trivalent constructs, expressing amongst others the NDV F protein gene or IBDV VP2 gene, suffered from severe disadvantages; they were either unable to replicate at all, or could only replicate for a limited number of cycles, or did not show expression of the heterologous inserts in vitro, and very few were effective in vivo, or provided adequate immune-protection. Genetic stability was poor in most cases tested. Therefore most were not suitable for the generation of effective vaccines based on recombinant npMDV.

Similarly, recombinant npMDV made out of the combination of known expression cassettes with single F protein or VP2 genes, were also not successful; either no progeny was generated, or no expression was seen, or the expression was lost quickly as a result of instability, leading to escape mutants (see Example 1, and FIG. 1).

To overcome these problems it was necessary to make unobvious choices and make selections and modifications that exceeded routine activities, in order to arrive at a recombinant npMDV for expression of both NDV F protein and IBDV VP2 protein, that did possess the desired levels of genetic stability, vector virus replicative ability, and consistent expression of the heterologous genes.

The inventors discovered that the use of too strong promoters caused instability in the multivalent expression cassette of the resulting npMDV vector, whereas too weak promoters did not induce enough expression or immune protection. Although they do not wish to be bound by theory, they speculate that the critical features making the recombinant npMDV according to the invention successful over prior art vectors, are: the selection of the specific promoters used, in combination with the modifications made to these promoters to regulate their relative strengths, and also the specific order of the heterologous genes expressed by these promoters, relative to each other in the expression cassette. This complex and specific combination of features provides a recombinant npMDV carrying a multivalent expression cassette with just the right balance in terms of stability, replicative capacity, and expression levels, to make this recombinant npMDV overcome all the biological hurdles it encounters in vitro and in vivo, and still be effective in immunising a target animal.

For the invention, a "recombinant" is a nucleic acid molecule or a micro-organism of which the genetic material has been modified, to result in a genetic make-up that it did not originally possess.

For the invention an "npMDV" is a virus from the MDV viral family that shows little or no pathogenicity to poultry. Preferably the npMDV are naturally occurring viruses, or viruses that have been attenuated by passageing, for example for use as vaccines. In a more preferred embodiment the npMDV are MDV2 or HVT viruses. Depending on the utility either of these can be more preferred, as they provide specific advantages: MDV2 is naturally more vireamic than HVT, so when a fast spread of the recombinant npMDV according to the invention is required, the preferred parental virus is an MDV2, more preferably of the SB1 strain. On the other hand, where the safety of the recombinant npMDV according to the invention is paramount, the HVT is the preferred parental virus, more preferably of the PB1 or FC-126 strain.

In an even more preferred embodiment, a combination of recombinant npMDV according to the invention is employed, wherein the parental viruses for the recombinant vector are of different type, for instance MDV2 and HVT. The advantage of this embodiment is the possibility to greatly enhance the number of immunogenic proteins that is presented and expressed into a target animal. Each vector can comprise a number of heterologous genes up to a certain maximum number where its stability, viral replication, and expression become affected. Therefore, a combination of vectors can deliver and present more heterologous genes than one type of vector alone. This combination of vectors from different type then overcomes the problem of the prior art where the inoculation of more than one vector of the same type leads to an overgrowth of one of these, so that immunisation is only achieved for the antigens from one of the vectors. By combining npMDV vectors according to the invention that are of different type, such as a combination of MDV2 and HVT based vectors, no significant overgrowth of one over the other occurs.

The term "comprising" (as well as variations such as "comprise", "comprises", and "comprised") as used herein, intends to refer to all elements, and in any possible combination conceivable for the invention, that are covered by or included in the text section, paragraph, claim, etc., in which this term is used, even if such elements or combinations are not explicitly recited; and not to the exclusion of any of such element(s) or combinations.

Therefore any such text section, paragraph, claim, etc., can therefore also relate to one or more embodiment(s) wherein the term "comprising" (or its variants) is replaced by terms such as "consist of", "consisting of", or "consist essentially of".

A gene is "heterologous" to the npMDV that carries it, if that gene was not present in the parental npMDV that was used to generate the recombinant npMDV vector according to the invention.

The term "gene" is used to indicate a nucleic acid that is capable of encoding a protein. A gene for the invention preferably encodes a complete protein, but may also encode a section of a protein, for example encoding only the mature form of a protein, i.e. without a 'leader', 'anchor', or 'signal sequence'. A gene may even encode a specific section of a protein, such as the section comprising an immunoprotective epitope.

In that regard a "protein" for the invention is a molecular chain of amino acids. The protein can be a native or a mature protein, a pre- or pro-protein, or a functional fragment of a protein. Inter alia: peptides, oligopeptides and polypeptides are included within the definition of protein.

For the invention, "comprising a heterologous nucleic acid molecule" relates to the insertion of the heterologous nucleic acid molecule into the genome of an npMDV. The insertion can be made by any available technique, provided the resulting recombinant npMDV is able to display its favourable effects of safe, stable and effective multivalent antigen expression.

The preferred insertion techniques are by cosmid regeneration, e.g. as described in WO 93/25.665, or by using bacmids, as described in EP 996.738. This essentially employs a set of large overlapping sub-genomic fragments of the npMDV genome to reconstruct a complete npMDV genome by cotransfection into host cells. As one of the cosmids carries an expression cassette, this becomes stably integrated into the genome of the (then recombinant) npMDV.

Figure 3:
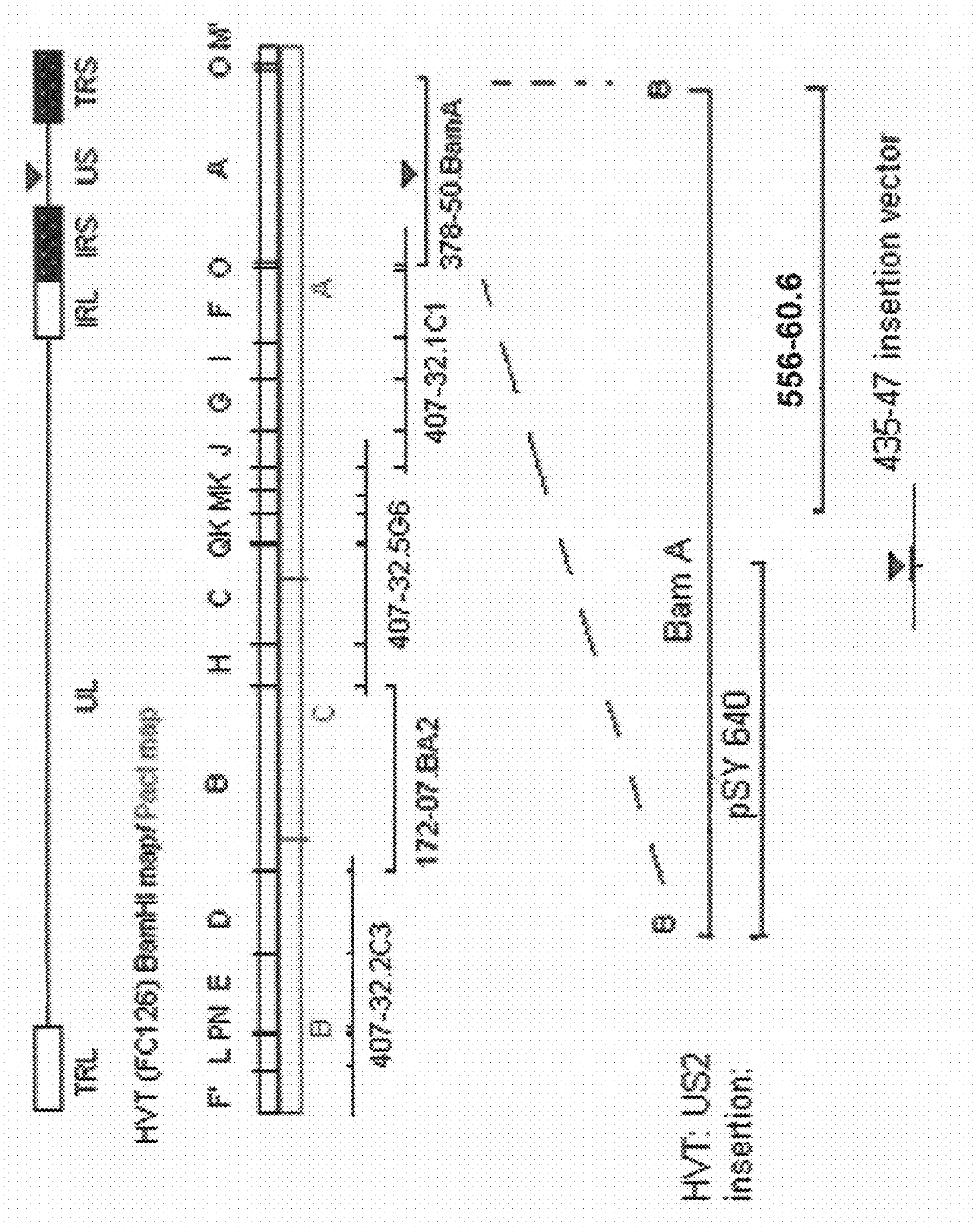

An outline of a protocol for transfection of a nucleic acid according to the invention into the genome of an HVT by cosmid regeneration is depicted in FIG. 3.

The term "in 5' to 3' direction", also known as: 'in downstream direction', is well known in the field. Together with the term "in this order" it serves to indicate the relative orientation which the elements that are summed up thereafter need to have in respect of each other, and in respect of the gene-expression machinery of the host cell in which the recombinant npMDV according to the invention will be replicated and expressed. As the skilled person will realise, this orientation relates to that DNA strand from the double stranded DNA genome of npMDV that is the 'coding strand', and it relates to the encoded mRNA molecule that is in the 'sense' orientation.

Nevertheless, and without prejudice to the section above: on the complementary strand of the DNA double helix, that is the 'template' strand, the relative order of the listed elements is the same, but the DNA strand orientation is from 3' to 5'.

Additionally, as will be apparent to a skilled person, because an expression cassette is a self contained expression module, the orientation of the whole of the expression cassette for the invention relative to the npMDV genome is not critical. That means that the nucleic acid molecule as a whole can be integrated into the npMDV genome in either of two orientations. For example when the nucleic acid molecule according to the invention is inserted in the Us region of the npMDV genome, it can be oriented to read towards the TRs or can be oriented to read towards the IRs. FIG. 1 in that respect only displays one of these two possible orientations.

A "promoter" for the invention is well known to be a functional region on the genome of an organism that directs the transcription of a downstream coding region. A promoter thus is a nucleic acid element, typically of DNA, that is situated upstream of an open reading frame, typically a gene.

A promoter initiates mRNA synthesis of the gene or coding region that it controls, starting from the 'transcription start site' (TSS). The mRNA produced is in turn translated into protein starting from the gene's startcodon, which is the first ATG sequence in the open reading frame (the first AUG in the mRNA). Typically the TSS is located at 30-40 nucleotides upstream of the start codon. A TSS can be determined by sequencing the 5' end of the mRNA of a gene, e.g. by the RACE technique.

In general promoters are comprised within 1000 nucleotides upstream of the position of the A of the startcodon, which is generally indicted as A+1, and most promoters are situated between −500 and A+1.

Commonly promoters contain a number of recognisable, regulatory regions, such as the enhancer area which is involved in regulation of the time, the duration, the conditions, and the level of transcription. The central promoter region is involved in the binding of transcription factors and directing the RNA polymerase. This generally contains a number of conserved sequence elements such as the TATA box, the CAAT box, and the GC box.

The nomenclature for a promoter is commonly based on the gene of which it controls the expression. For example, the term 'hCMV-IE1 gene promoter', refers to the promoter that in nature drives the expression of the IE1 gene from hCMV, and is situated immediately upstream of that gene. Because the IE1-gene is such a well documented and clearly recognisable gene, and because the genomes of many herpesvirideae have been sequenced (in whole or in part), such a promoter can readily be identified by routine techniques. For example, a promoter can simply be selected by roughly subcloning the region in between two consecutive genes, e.g. from the poly A signal of an upstream gene to the TSS of a downstream gene. The promoter is then identified by standard tests: the expression of a marker gene by subcloned smaller or larger sections of a suspected promoter.

Consequently, an "hCMV-IE1" gene promoter is well known in the art, and can be readily obtained from a variety of commercial sources, such as from suppliers of commercial plasmids for cloning and expression. The IE1 gene is also called the major IE gene. Commonly, this hCMV-IE1 gene promoter is about 1.5 kb in size and consists of an enhancer, a promoter, and an intron, whereby the promoter activity proceeds into the intron region. A detailed study of the hCMV-IE1 enhancer-promoter region is described by Koedood et al. (1995, J. of Virol., vol. 69, p. 2194-2207). An hCMV-IE1 gene promoter can for example be derived from the plasmid pl17 as described by Cox et al. (2002, Scand. J. Immunol., vol. 55, p. 14-23), or from mammalian expression vectors such as the pCMV (Clontech), or pCMV-MCS (Stratagene; Genbank™ accession nr. AF369966) series. Alternatively, the promoter can be obtained from the genome of an hCMV virus, from the area preceding the IE1 gene, using routine molecular biological tools and methods.

For the invention, the prior art hCMV-IE1 gene promoter was not effective, as it did not display the desired strength and stability in the context of an npMDV vector, and in an expression cassette from which a further heterologous gene is being expressed. Surprisingly it was found that by using a specific central part of the hCMV-IE1 gene promoter, the "core" promoter (element a.), the desired characteristics were achieved. In a specific embodiment, this core promoter is only about 361 bp in size, and is presented in SEQ ID NO: 1.

Nevertheless, of the hCMV-IE1 gene core promoter, many highly similar versions are known; for example a search against NCBI's Genbank™ using a Blast alignment with SEQ ID NO: 1 as query, displays over 60 similar promoter sequences that are within the 95% identity level. These homologs and variants of the hCMV-IE1 promoter are equally usable for the invention, provided a similar core section of this promoter is being used.

Therefore, in a preferred embodiment the hCMV-IE1-gene core promoter for the invention is a nucleic acid molecule of about 361 basepairs, comprising a nucleotide sequence that has at least 95% nucleotide sequence identity to the full length of the nucleotide sequence in SEQ ID NO: 1. More preferred is a nucleotide sequence identity of at least 96, 97, 98, 99 or even 100%, in that order of preference.

As the skilled person is well aware, some variance in length may occur, either of the hCMV-IE1-gene core promoter but also of the other elements that make up the heterologous nucleic acid molecule inserted in the recombinant npMDV according to the invention. This can result from differences in the exact conditions that are used for cloning and construction; for example from using different restriction enzyme sites, PCR cloning primers, or different conditions for adapting the ends of the cloning molecules used. Consequently, some variation in length of the constituting elements may occur.

Therefore, for the invention "about 361" is: 361±25%, preferably ±20, 15, 12, 10, 8, 6, 5, 4, 3, 2, 1 or even 0%, in that order of preference.

This however under the proviso that such length differences do not affect the stability and efficacy of the overall heterologous nucleic acid molecule insert, then these length differences are immaterial, and are considered part of the invention.

A promoter for the expression of a heterologous gene in a (virus) vector needs to be able to effectively drive the transcription of that downstream coding region. This is commonly referred to as the promoter being "operatively linked" to the gene, or: the gene being "under the control of" the promoter. This commonly means that in the expression cassette the promoter and the gene are connected on the same DNA, in effective proximity, and with no signals or sequences between them that would intervene with an effective transcription and translation.

Therefore, in a preferred embodiment, the hCMV-IE1 gene core promoter for the invention is "operatively linked" to the downstream gene for the NDV F protein.

The "NDV F protein gene" for the invention (element b.) encodes a fusion protein from an NDV. Such genes are well known and their sequence information is extensively available in the prior art, from a variety of commonly available plasmid constructs. Alternatively, it can be obtained from an NDV isolated from nature, using routine techniques for manipulating an RNA virus. NDV virus can be readily identified using serology, or molecular biology.

The F protein gene used for the invention was derived from NDV Clone 30, a common lentogenic NDV vaccine strain; the gene's sequence is presented in SEQ ID NO: 2. For the invention homologs and variants of the F protein gene would equally be applicable, either from lentogenic, mesogenic of velogenic NDV, as the F protein gene sequence itself is highly conserved in these different NDV pathotypes.

Therefore, for the invention the NDV F protein gene preferably is a nucleic acid molecule comprising a nucleotide sequence that has at least 90% nucleotide sequence identity to the full length of the nucleotide sequence as in SEQ ID NO: 2. More preferred is a nucleotide sequence identity of at least 92, 94, 95, 96, 97, 98, 99 or even 100%, in that order of preference.

Alternatively, to further improve the immune-efficacy of the heterologous protein expressed from a nucleic acid molecule according to the invention, the heterologous gene can be subjected to codon optimisation. The process of codon optimisation is well known in the art, and involves the adaptation of a nucleotide sequence encoding a protein to encode the same amino acids as the original coding sequence, be it with other nucleotides; i.e. the mutations made are essentially silent. This can improve the level at which the coding sequence is expressed in a biological context that differs from the origin of the expressed gene.

The inventors have found that to achieve the desired stability of replication and efficiency of expression, it is necessary to deliberately separate the transcription of the two heterologous genes in the nucleic acid molecule according to the invention, thus generate two separate mRNA's. Therefore a transcription terminator needs to be introduced in between the two coding regions, downstream of the NDV F protein gene and upstream of the Ch β-actin gene core promoter.

A "transcription terminator" (element c.) is well known to be a regulatory nucleic acid region, which causes the termination of the transcription of a coding DNA sequence, by RNA polymerase. Typically 'intrinsic termination' is caused by a stem-loop structure in the generated mRNA, comprising a G-C rich sequence followed by a U rich sequence. Most genes comprise a transcription terminator at the downstream end of their coding sequence, and for the invention it is not critical which terminator is used, provided that effective transcription termination of the upstream F protein gene is achieved, and 'read-through' transcription into the VP2 coding region is prevented. One example of a convenient transcription terminator that can be used for the invention is the hCMV-IE1 gene transcription terminator, described in SEQ ID NO: 3.

A "chicken beta-actin gene promoter" (Ch β-actin gene promoter) is well known in the prior art, and many plasmid constructs and commercial expression vectors employ this promoter. It was first described by Kost et al. (1983, Nucl. Acids Res., vol. 11, p. 8287-8301), see Genbank acc. nr: X00182. Subsequently many variants were made, such as a hybrid promoter (Tsukamoto et al., 2002, J. of Virol., vol. 76, p. 5637-5645). In EP 351.585 the inventors modified a Ch β-actin gene promoter to make it up to 10 times more productive, by exchanging a splice acceptor site: the original splice acceptor site that sits at −7 in the Ch β-actin gene promoter was replaced by a splice acceptor site from the third intron of the rabbit globin gene; the resulting modified Ch β-actin gene promoter is described in Genbank acc. nr.: E03011, and is used in a plasmid described in Genbank acc. nr.: AJ575208.

For the present invention this modified Ch β-actin gene promoter was tested, but it was ineffective; it required a further significant adaptation to provide the desired balance of strength and stability, for use in the context of an npMDV multivalent expression vector. This was achieved by deleting a large part of the intron in this Ch β-actin gene promoter. The resulting adapted promoter comprising only the core region of this promoter, is the Ch β-actin gene core promoter (element d.), which is about 696 bp in size, and is presented as SEQ ID NO.: 4.

Nevertheless, like the situation for the modified hCMV-IE1 gene core promoter described above, many highly similar versions of the Ch β-actin gene core promoter are known. Such homologs and variants of the Ch β-actin gene core promoter are equally usable for the invention, provided a similar core section of this promoter is being used.

Therefore, in a preferred embodiment the Ch β-actin gene core promoter for the invention is a nucleic acid molecule of about 696 basepairs, comprising a nucleotide sequence that has at least 95% nucleotide sequence identity to the full length of the nucleotide sequence in SEQ ID NO: 4. More preferred is a nucleotide sequence identity of at least 96, 97, 98, 99 or even 100%, in that order of preference.

As discussed above, length differences that do not affect the stability and efficacy of the overall nucleic acid molecule according to the invention, are considered part of the invention. Therefore, for the invention "about 696" is: 696±25%, preferably ±20, 15, 12, 10, 8, 6, 5, 4, 3, 2, 1 or even 0%, in that order of preference.

The Ch β-actin gene core promoter according to the invention needs to be "operatively linked" to the downstream classic IBDV VP2 gene.

The "classic type IBDV VP2 gene" for the invention (element e.) encodes a VP2 protein from an IBDV that is of the classic type. Such genes are well known and their sequence information is readily available in the prior art, see e.g. Genbank acc. nr: D00869 (F52/70), D00499 (STC) or AF499929 (D78). Alternatively, this gene can be obtained from the genome of a classic IBDV isolated from nature, using routine techniques for manipulating a Birnavirus. Classic type IBDV's can be readily identified using serology, or molecular biology.

The VP2 gene used for the invention was derived from the classic IBDV strain Faragher 52/70; the gene's sequence is presented in SEQ ID NO: 5. For the invention homologs and variants of a VP2 gene would equally be applicable, provided they are of the classic serotype.

Because such VP2 protein genes commonly share more than 90% nucleotide sequence identity, therefore, for the invention the classic IBDV VP2 gene preferably is a nucleic acid molecule comprising a nucleotide sequence that has at least 90% nucleotide sequence identity to the full length of the nucleotide sequence as in SEQ ID NO: 5. More preferred is a nucleotide sequence identity of at least 92, 94, 95, 96, 97, 98, 99 or even 100%, in that order of preference.

The recombinant npMDV according to the invention can be produced by common techniques, mainly by amplification in in vitro cultures of primary chicken cells, typically chicken embryo fibroblast cells (CEF's). These can be prepared by trypsinisation of chicken embryos. The CEF's are plated in monolayers and infected with the npMDV. This process can be scaled up to industrial sized production.

Typically, the infected host cells are harvested while still intact, to obtain the recombinant npMDV in its cell-associated form. These cells are taken up in an appropriate carrier composition to provide stabilisation for storage and freezing. Next the infected cells are commonly filled into glass ampoules, which are sealed, frozen and stored in liquid nitrogen. This way they can be transported to users across the world in so-called 'cold chain' logistics.

In situations where a cold chain is not feasible, and the npMDV according to the invention is a recombinant HVT, an alternative is to use freeze drying. This employs the favourable characteristic of HVT that it can be isolated from its host cell, for instance by sonication at the end of culturing, taken up into a stabiliser, and freeze dried for stable storage.

In a preferred embodiment of the recombinant npMDV according to the invention, a further genetic element is comprised in the expression cassette: an additional transcription terminator (element f.) is present downstream of the classic IBDV VP2 gene in the nucleic acid according to the invention. This serves to guarantee transcription termination of the VP2 gene expression, independent of the composition of the region of the npMDV genome that flanks the 3' side of the expression cassette.

The transcription terminator downstream of VP2 (element f.) may be the same or different compared to the terminator downstream of the F protein gene (element c.), as long as proper transcription termination is provided and stability and expression are not affected.

In a further preferred embodiment, the transcription terminator at the 3' side of the classic IBDV VP2 gene in the nucleic acid according to the invention (element f.), is derived from Feline herpes virus 1 (FHV1), from the FHV1 Us/TRs junction, downstream of FHV1 Us9. This is described for example in Genbank acc. nr: D42113, and the sequence used for one embodiment of the invention is presented in SEQ ID NO: 6.

Figure 2:
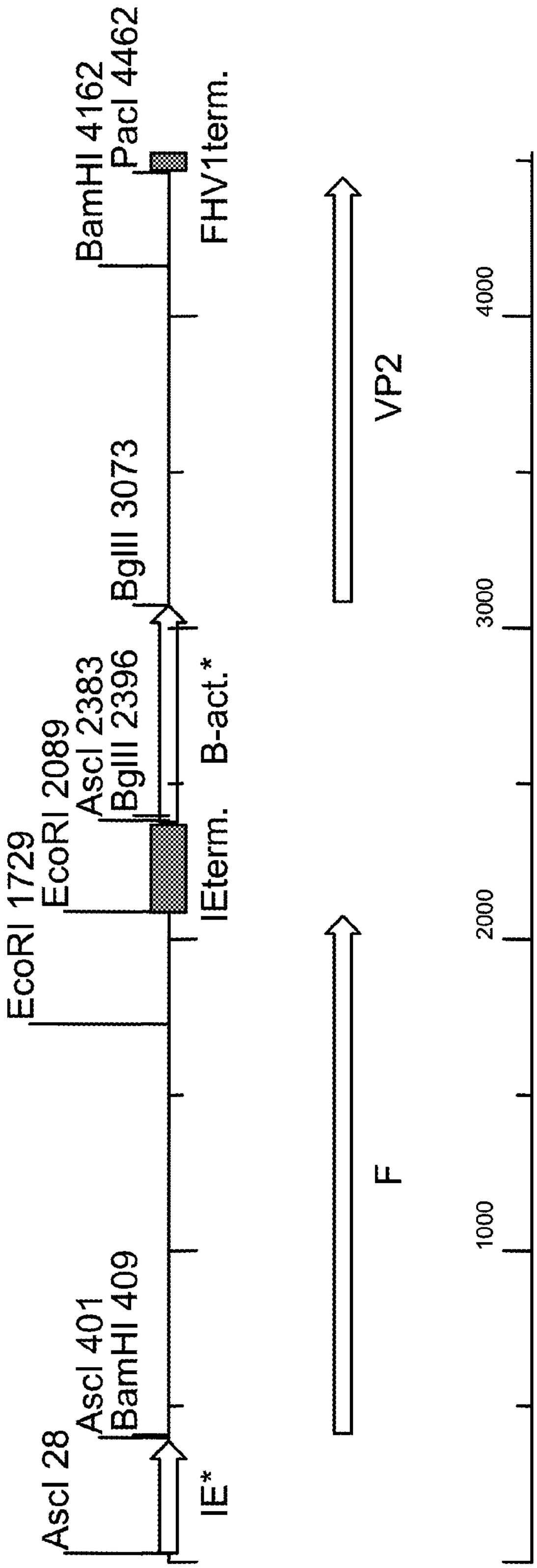

In a preferred embodiment, the recombinant npMDV according to the invention comprises a nucleotide sequence as presented in SEQ ID NO: 7, and as depicted in FIG. 2.

It is noted that the sequence provided in SEQ ID NO: 7 is the actual nucleotide sequence that was determined for the expression cassette from the recombinant npMDV construct HVP309, that had been amplified for 6 tissue culture passages from a plaque selected after transfection.

Therefore, in a further aspect, the invention relates to a nucleic acid molecule for use in the construction of a recombinant npMDV according to the invention, said nucleic acid molecule comprising in 5' to 3' direction, and in this order:

a. an hCMV-IE1 core promoter,
b. an NDV F protein gene,
c. a transcription terminator,
d. a chicken beta-actin gene core promoter,
e. a classic type IBDV VP2 gene,
f. a transcription terminator.

The nucleic acid molecule according to the invention is the expression cassette for the invention. In a preferred embodiment, the nucleic acid molecule according to the invention has a nucleotide sequence as presented in SEQ ID NO: 7.

The generation, construction and assembly of the recombinant npMDV, the nucleic acid molecule, and the recombinant DNA molecule, all according to the invention, can be done by well-known molecular biological techniques, involving cloning, transfection, recombination, selection, and amplification.

These, and other molecular biological techniques are explained in great detail in standard text-books like Sambrook & Russell: "Molecular cloning: a laboratory manual" (2001, Cold Spring Harbour Laboratory Press; ISBN: 0879695773); Ausubel et al., in: Current Protocols in Molecular Biology (J. Wiley and Sons Inc, NY, 2003, ISBN: 047150338X); C. Dieffenbach & G. Dveksler: "PCR primers: a laboratory manual" (CSHL Press, ISBN 0879696540); and "PCR protocols", by: J. Bartlett and D. Stirling (Humana press, ISBN: 0896036421).

For the convenient construction of the nucleic acid molecule according to the invention, and for its use to generate a recombinant npMDV according to the invention, the nucleic acid can itself be comprised in a larger nucleic acid molecule.

Therefore, in a further aspect, the invention relates to a recombinant DNA molecule comprising the nucleic acid molecule according to the invention.

Preferably such a recombinant DNA molecule according to the invention is a common cloning plasmid, e.g. such as derived from pBR322, or pUC, series. These are widely commercially available.

When the recombinant DNA molecule according to the invention is set up for use in transfection protocols, it is commonly referred to as a 'transfervector', 'shuttle vector', or 'donor plasmid'. In this situation the nucleic acid molecule according to the invention may be flanked on both sides by sequences that are derived from the npMDV genome. These allow for homologous recombination, and direct the insertion (in a desired orientation) to the target genetic insertion locus on the npMDV genome.

Alternatively, the recombinant DNA molecule according to the invention may be a cosmid construct, for use in cosmid regeneration.

Typically, a transfervector that is used in transfection is not itself integrated into the genome of the live recombinant carrier micro-organism; it only facilitates the integration of the expression cassette it carries.

Figure 4:
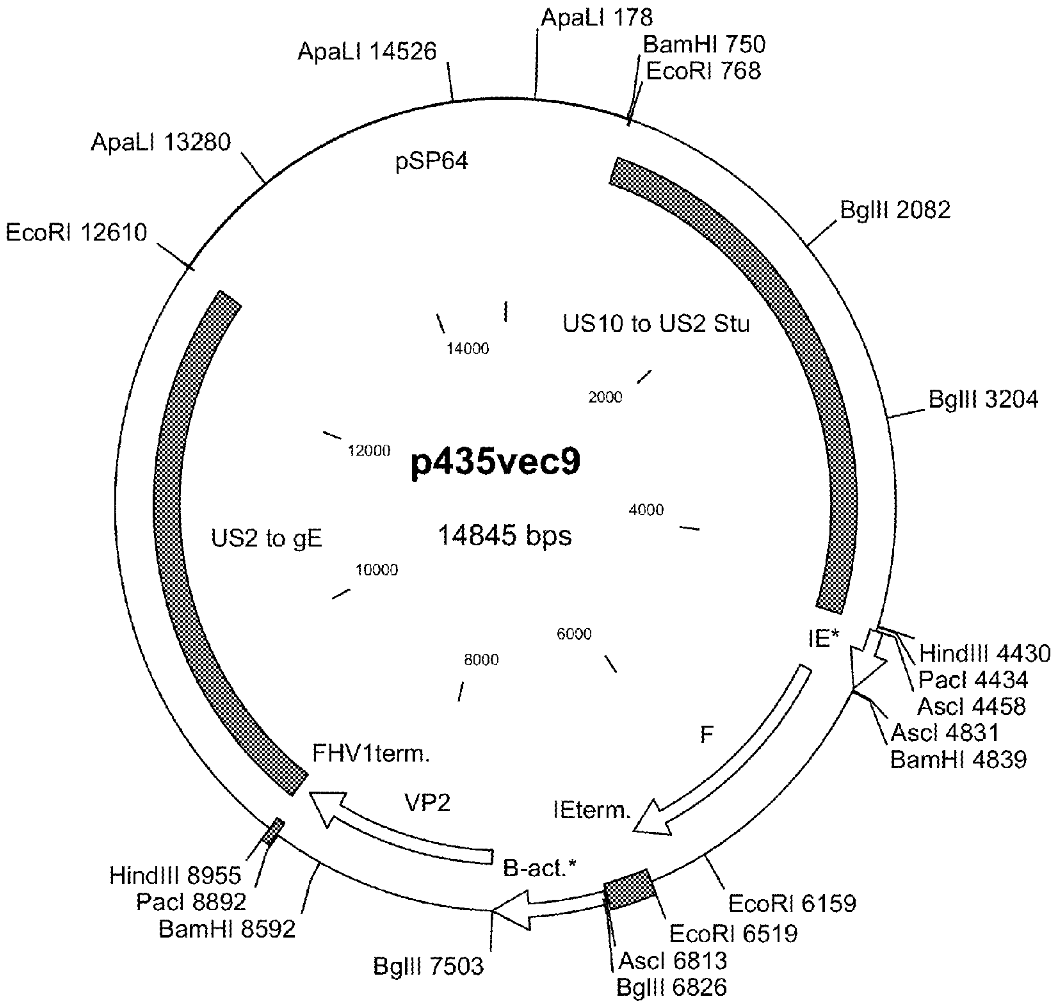

An example of a recombinant DNA molecule according to the invention, which serves as a transfer vector for the invention is plasmid p435vec9, depicted in FIG. 4.

The recombinant npMDV according to the invention comprises the nucleic acid molecule according to the invention in a single genetic insertion locus. Many insertion loci are known for npMDV, and in principle these are all suitable for use in the invention, provided the inserted multivalent expression cassette is able to display its stable and effective properties. For practical reasons, certain loci are preferred, for example because the necessary molecular biological tools for construction and analysis are available. In this regard, for the present invention the use of a genetic insertion locus in the Us region of the npMDV genome is preferred.

Therefore, in a preferred embodiment of the recombinant npMDV according to the invention, the heterologous nucleic acid molecule is inserted into the genome of the recombinant npMDV in the Us region.

Particularly stable and effective npMDV recombinants for the invention could be made by employing as the single genetic insertion locus for the invention, the Us2 gene or the Us10 gene of the npMDV genome.

Therefore, in a preferred embodiment of the recombinant npMDV according to the invention, the heterologous nucleic acid molecule is inserted into the genome of the recombinant npMDV in the Us2 gene or in the Us10 gene.

For the invention the terms "in the Us2 gene" and "in the Us10 gene" intend to indicate that an insertion has been made in the region of the npMDV genome comprising the Us2 or Us10 gene; this can refer to the promoter, or to the coding region of either of these genes. Also, the netto effect of the insertion may itself be an insertion, deletion, or neutral replacement, as described. An expected consequence of such insertion is that the normal coding function of the Us2 or Us10 gene is disturbed in the resulting recombinant npMDV.

The recombinant npMDV according to the invention is a live recombinant carrier micro-organism, or a "vector" virus, which is advantageously used for poultry vaccination. In this utility it is safe, as it does not cause a negative vaccination reaction, such as any signs of disease or infection, or reduction in growth or development of the inoculated animal, even when applied at very young age. Further, the recombinant npMDV is stable in replication, either in cell-culture (in vitro), or in a target animal (in vivo). Also, the recombinant npMDV provides a strong and consistent expression (both in vitro and in vivo) of the two heterologous genes it carries: the NDV F protein gene, and the classic IBDV VP2 gene. Finally, through its replication and expression in a target animal, it provides for an effective presentation of the expressed heterologous genes to the target's immune system. This generates an efficacious immune response that protects the vaccinated target animal against infection and/or disease caused by NDV and IBDV. In addition, the npMDV recombinant provides for immune-protection against MDV.

Being "stable" for the invention means that the genetic make-up of the recombinant npMDV according to the invention does not significantly change in subsequent rounds of virus replication; in practice this would mean the loss of expression of one or both inserted heterologous gene(s). This can for example conveniently be monitored with routine techniques, e.g. by subjecting the recombinant npMDV according to the invention to subsequent passageing in cell culture, followed by a passage in animals. Re-isolated virus is then plated in cell culture dishes, covered with agar, and incubated until plaques become visible; all using routine techniques. Next the plaques are stained for expression of the F or the VP2 protein using suitable antibody preparations in an immunofluorescence assay (IFA) protocol. The number of plaques that no longer express one or both proteins is recorded, whereby at least 100 individual plaques should be monitored e.g. by UV-microscopy.

A stringent stability test is to apply 15 consecutive tissue culture passages, followed by an inoculation into target animals to assess the remaining potency in a challenge-infection experiment.

As a skilled person will appreciate, under such circumstances of intensive passageing, an absolute (100%) stability can not be guaranteed, as some level of natural background mutation may always occur. This is not a sign of significant instability; in fact a recombinant vector virus displaying better than 95% genetic stability is in principle suitable for vaccine production and use in target animals, although much better stability is achieved in the present case.

It was surprisingly found that the recombinant npMDVs according to the invention in a stringent stability test as described above, maintained stable expression of both heterologous genes in more than 95% of the re-isolated plaques. In fact, in several tests only a very low percentage of plaques (between 0% and 0.3%) were found not to be expressing one of the heterologous genes anymore (Example 5). Also, when these passaged recombinant npMDVs were tested in target animals, they were still capable of providing excellent immune protection, both against NDV and against IBDV infection (Examples 6 and 7).

This is a strong improvement over results found with prior art npMDV recombinants, and unsuccessful recombinants made and tested in the course of the experiments for the invention (see Example 1). Such unsuccessful recombinant npMDVs often did not yield plaques after transfection that could be amplified for a number of rounds, or showed only very weak expression of the heterologous protein, or were losing expression after a few rounds of amplification. Some constructs could be amplified for testing in animals, but did not provide an immune response, as most of these recombinant npMDVs upon re-isolation were found to have lost the ability to express (one of) the heterologous genes.

Therefore in a preferred embodiment, the recombinant npMDV according to the invention is characterised in that more than 95% of said recombinant viruses maintain the expression of both heterologous proteins after 15 consecutive passages in cell culture.

In further preferred embodiments more than 96, 97, 98, 99, 99.5, 99.7, or 100% of the recombinant viruses maintained the expression of both heterologous proteins, in that order of preference.

By methods of transfection, such as the cosmid regeneration as described above and exemplified hereinafter, the nucleic acid molecule, and/or the recombinant DNA molecule according to the invention can be used to obtain the recombinant npMDV according to the invention, comprising the nucleic acid molecule according to the invention stably integrated in a single genetic insertion locus on its genome.

Therefore, a further aspect of the invention relates to a method for the preparation of the recombinant npMDV according to the invention, said method comprising the insertion of the nucleic acid molecule according to the invention into a single genetic insertion locus on the genome of an npMDV.

The insertion of the nucleic acid molecule according to the invention into an npMDV genome to generate the recombinant npMDV according to the invention can conveniently be performed by using the recombinant DNA molecule according to the invention as transfer vector.

Although the direct insertion of the complete nucleic acid molecule according to the invention into an npMDV genome is the preferred method to generate a recombinant npMDV according to the invention, there are other well known ways in which such a recombinant npMDV can be generated. For example by inserting parts of the nucleic acid molecule according to the invention into npMDV, in single or in multiple round(s) of transfection. These parts can be devised in such a way that upon integration of all parts, the total insert forms the complete expression cassette for the invention, for example by employing overlapping regions to steer the order and the orientation of the parts.

As described, npMDV is commonly amplified in cultures of primary cells, and the resulting npMDV vaccine can be supplied as cell-free product, or (in the case of HVT as parental virus) stored in freeze dried form. However, and preferably npMDV vaccine is supplied as cell-bound product, comprising harvested CEF cells that are infected with npMDV.

Similarly, the nucleic acid- and the recombinant DNA molecules according to the invention, for example in the form of plasmids are commonly amplified by introducing them into bacterial cells which then provide replication and amplification; cosmids can be amplified using lambda phages. For example special laboratory strains of *Escherichia coli* bacteria are commonly applied, and widely available from commercial suppliers. Conveniently these can be purchased as competent cells, ready for introduction of DNA by common techniques such as electroporation or heat shock.

Therefore, in a further aspect the invention relates to a host cell comprising the recombinant npMDV, the nucleic acid molecule, or the recombinant DNA molecule, all according to the invention.

A "host cell" for the invention is preferably an *E. coli* bacterial cell for use with the nucleic acid- or the recombinant DNA molecules according to the invention. Also, a host cell for the invention is preferably a CEF for use with a recombinant npMDV according to the invention.

As described, the advantageous use of the recombinant npMDV according to the invention, is in a vaccine for poultry.

Therefore in a further aspect the invention relates to a vaccine for poultry, comprising the recombinant npMDV or the host cell, both according to the invention, and a pharmaceutically acceptable carrier.

A "vaccine" is well known to be a composition comprising an immunologically active compound, in a pharmaceutically acceptable carrier. The 'immunologically active compound', or 'antigen' is a molecule that is recognised by the immune system of the target and induces an immunological response. The response may originate from the innate or the acquired immune system, and may be of the cellular and/or the humoral type.

A vaccine induces an immune response that aids in preventing, ameliorating, reducing sensitivity for, or treatment of a disease or disorder resulting from infection with a micro-organism. The protection is achieved as a result of administering at least one antigen derived from that micro-organism. This will cause the target animal to show a reduction in the number, or the intensity, of clinical signs caused by the micro-organism. This may be the result of a reduced invasion, colonization, or infection rate by the micro-organism, leading to a reduction in the number or the severity of lesions and effects that are caused by the micro-organism or by the target's response thereto.

The term "poultry" for the invention relates to any species of bird susceptible to inoculation with npMDV; the preferred target species are chicken, turkey, and duck; with chickens as most preferred species.

The target birds may be layers, breeders, combination breeds, or parental lines of any of such breeds.

The age, weight, sex, immunological status, and other parameters of the poultry to be vaccinated are not critical, although it is evidently favourable to vaccinate healthy targets, and to vaccinate as early as possible to prevent (the consequences of) any field infection.

The vaccine according to the invention is preferably applied in the cell-associated form, whereby host cells that are infected with such a recombinant npMDV are inoculated into the target animal.

The "pharmaceutically acceptable carrier" is intended to aid in the stabilisation and administration of the vaccine, without causing (severe) adverse effects to the health of the target animal to which it is administered. Such a carrier can for instance be sterile water or a sterile physiological salt solution. In a more complex form the carrier can e.g. be a buffer, which can comprise further additives, such as stabilisers or conservatives. Details and examples are for instance described in well-known handbooks such as: "Remington: the science and practice of pharmacy" (2000, Lippincott, USA, ISBN: 683306472), and: "Veterinary vaccinology" (P. Pastoret et al. ed., 1997, Elsevier, Amsterdam, ISBN 0444819681).

For the present invention, when the vaccine is cell-based, then the carrier is preferably a mixture of culture medium with serum (about 10%) and DMSO (about 6%). The serum can be any serum routinely used for cell culturing such as foetal- or newborn calf serum.

The vaccine according to the invention is prepared from live recombinant npMDV according to the invention by methods as described herein, which are readily applicable by a person skilled in the art. For example, the recombinant npMDV according to the invention is constructed by transfection and recombination and the desired recombinant npMDV is selected as described herein. Next the recombinant npMDV vector viruses are produced industrially in smaller or larger volumes. Although production in host animals is possible, proliferation in in vitro cultures, e.g. in CEF's, is preferred. From such cultures a suspension comprising the virus is harvested, either as whole cells or as a cell-sonicate, this suspension is formulated into a vaccine and the final product is packaged. After extensive testing for quality, quantity and sterility such vaccine products are released for sale.

General techniques and considerations that apply to the preparation of vaccines are well known in the art and are described for instance in governmental regulations (Pharmacopoeia) and in handbooks such as: "Veterinary vaccinology" and: "Remington" (both supra).

The vaccine according to the invention in principle can be given to target poultry by different routes of application, and at different points in their lifetime, provided the inoculated recombinant npMDV can establish a protective infection.

However, because an infection with MDV, NDV or IBDV can be established already at very young age, it is advantageous to apply the vaccine according to the invention as early as possible. The vaccine according to the invention is preferably applied at the day of hatch ("day 1"), or in ovo, e.g. at 18 days ED. Suitable equipment for automated injection into the egg at industrial scale is available commercially. This provides the earliest possible protection, while minimising labour cost.

Therefore, in a preferred embodiment, the vaccine according to the invention is administered in ovo.

Different in ovo inoculation routes are known, such as into the yolk sac, the embryo, or the allantoic fluid cavity; these can be optimised as required. Preferably in ovo inoculation is performed such that the needle actually touches the embryo.

Alternatively, a parenteral inoculation of individual young birds can be applied. This is preferably applied intramuscular or subcutaneous.

Formulations of the vaccine according to the invention suitable for injection, are e.g. a suspension, solution, dispersion, or emulsion.

Depending on the route of application of the vaccine according to the invention, it may be necessary to adapt the vaccine composition. This is well within the capabilities of a skilled person, and generally involves the fine-tuning of the efficacy or the safety of the vaccine. This can be done by adapting the vaccine dose, quantity, frequency, route, by using the vaccine in another form or formulation, or by adapting the other constituents of the vaccine (e.g. a stabiliser or an adjuvant).

For example, to be suitable for application in ovo, the vaccine composition is required to be very mild, in order not to reduce the hatchability of the eggs. However, even then some reduction in hatchability may still occur, e.g. resulting from mechanical damage to the embryo by the inoculation itself, infection, etc.

In addition to the genetic stability provided by the nucleic acid molecule according to the invention, the safety of the vaccine according to the invention is also provided by employing as the parental virus for the recombinant npMDV according to the invention, an established safe npMDV vaccine strain, for example the HVT vaccine strains PB1 or FC-126. Alternatively the MDV2 vaccine strain SB1. All these are generally available (FC-126 from ATCC: VR #584-C; and PB1 and SB1 are commercialised by MSD Animal Health) and known to be suitable for inoculation of young birds or embryos. The incorporation of a heterologous nucleic acid does not increase the virulence or pathogenicity of the parental npMDV (on the contrary), and no reversion to virulence is to be expected, as npMDV are naturally apathogenic.

The exact amount of recombinant npMDV according to the invention per animal dose of the vaccine is not as critical as it would be for an inactivated type vaccine; because the recombinant npMDV is alive, it will replicate itself and thus multiply in the target animal up to a level of viremia that is biologically sustainable. In principle the vaccine dose only needs to be sufficient to initiate such a productive infection. A higher inoculum dose does not shorten the time it takes to reach an optimal vireamic infection in the host. Therefore, very high doses are not effective in that the viremia cannot be higher than the natural equilibrium, and in addition such a very high inoculum dose is not attractive for economic reasons.

A preferred inoculum dose is therefore between 1×10^2 and 1×10^6 plaque forming units (pfu) of npMDV vector viruses per animal-dose, more preferably between 1×10^2 and 1×10^5 pfu/dose, even more preferably between 1×10^3 and 1×10^4 pfu/dose; most preferably between 1500 and 5000 pfu/dose. When the vaccine according to the invention is cell-associated, these numbers of recombinant npMDV are comprised in infected host cells. In that case one animal dose comprises between 100 and 10.000 infected host cells, preferably 100-5000 infected cells per dose, more preferably: 200-2000 infected cells per dose.

Methods to count viral particles of the recombinant npMDV according to the invention are well known.

Determination of what is an immunologically effective amount of the vaccine according to the invention is well within reach of the skilled person, for instance by monitoring the immunological response following vaccination, or after a challenge infection, e.g. by re-isolation of the pathogen, or by monitoring the targets' clinical signs of disease, or serological parameters, and comparing these to responses seen in mock-vaccinated animals.

The dosing scheme for applying the vaccine according to the invention to a target organism can be in single or multiple doses, which may be given at the same time or sequentially, in a manner compatible with the formulation of the vaccine, and in such an amount as will be immunologically effective.

The vaccine according to the invention can be used for prophylactic and/or for therapeutic treatment, and so interferes either with the establishment and/or with the progression of an infection or its clinical symptoms of disease.

The vaccine according to the invention may effectively serve as a priming vaccination, which can later be followed and amplified by a booster vaccination, for instance once again with the same vaccine, or with a classical inactivated and adjuvanted whole virus vaccine.

The protocol for the administration of the vaccine according to the invention ideally is integrated into existing vaccination schedules of other vaccines.

Preferably the vaccine according to the invention is applied only once, either at the day of hatch, or in ovo at day 18 ED.

The volume per animal dose of the recombinant npMDV according to the invention can be optimised according to the intended route of application: in ovo inoculation is commonly applied with a volume between 0.05 and 0.5 ml/egg, and parenteral injection is commonly done with a volume between 0.1 and 1 ml/bird.

The optimisation of the vaccine dose volume is well within the capabilities of the skilled artisan.

It goes without saying that admixing other compounds, such as stabilisers, carriers, diluents, emulsions, and the like to vaccines according to the invention are also within the scope of the invention. Such additives are described in well-known handbooks such as: "Remington", and "Veterinary Vaccinology" (both supra).

With the proper optimisation of formulation, dose and application, as described above, the vaccine according to the invention is able to protect poultry against MDV, NDV and IBDV from a single inoculation at very young age. Because npMDV provides a persistent infection, the protection provided has excellent duration of immunity which lasts well unto the onset of lay, at about 20-25 weeks of age. The effectivity of protection can be assessed in different ways, such as clinical scoring, serology, (histo-) pathology etc.

The vaccine according to the invention effectively is a 'marker vaccine' for NDV and for IBDV, because the immunity it generates is only directed against one protein from these viruses. This allows the "differentiation of infected and vaccinated animals", the so-called DIVA approach. This can conveniently be detected by a serological assay such as an ELISA or immuno-fluorescence assay.

Apart from the multivalent immune protection that the vaccine according to the invention provides (against NDV, and IBDV; and in addition to that against MDV), it is advantageous to make further combinations by adding further antigenic compounds, in order to enhance the immune protection already provided or to expand to other pathogens. In principle this can be any live or killed micro-organisms or subunit antigen, provided this does not negatively interfere with the safety, stability, and efficacy of the vaccine according to the invention.

Therefore, in a preferred embodiment, the vaccine according to the invention comprises at least one additional immunoactive component.

Such an "additional immunoactive component(s)" may be an antigen, an immune enhancing substance, a cytokine, and/or a vaccine. This provides advantages in terms of cost, efficiency and animal welfare. Alternatively, the vaccine according to the invention, may itself be added to a vaccine.

In a more preferred embodiment the at least one additional immunoactive component is a micro-organism pathogenic to poultry; the micro-organism can itself be a recombinant organism, e.g. expressing an immunoprotective protein. Alternatively, the at least one additional immunoactive component is a (sub-unit) antigen which is derived from a micro-organism pathogenic to poultry. This can be 'derived' in any suitable way, for instance from an extract or homogenate of a micro-organism, or as the product from a recombinant expressed nucleic acid, which nucleic acid had been derived from a region encoding an antigenic protein from a micro-organism pathogenic to poultry.

The additional micro-organism is preferably selected from the following groups, and/or the additional antigen is preferably derived from a micro-organism selected from the following groups, consisting of:

viruses: infectious bronchitis virus, NDV, Adenovirus, Egg drop syndrome virus, IBDV, chicken anaemia virus, avian encephalo-myelitis virus, fowl pox virus, turkey rhinotracheitis virus, duck plague virus (duck viral enteritis), pigeon pox virus, MDV, avian leucosis virus, ILTV, avian pneumovirus, and Reovirus;

bacteria: *Escherichia coli, Salmonella* spec., *Ornitobacterium rhinotracheale, Haemophilis paragallinarum, Pasteurella multocida, Erysipelothrix rhusiopathiae, Erysipelas* spec., *Mycoplasma* spec., and *Clostridium* spec.;

parasites: *Eimeria* spec.; and fungi: e.g. *Aspergillus* spec.

In more preferred embodiments of the vaccine according to the invention, the additional immunoactive component is selected from the group of MDV, NDV and IBDV, or from any combination thereof. Such additional component serves to improve and expand the immunogenicity provided. This is advantageous in those cases or geographic regions where very virulent field strains of MDV, NDV or IBDV are prevalent.

In this regard, the combination of an npMDV with an MDV1, MDV2, or HVT is known; for the invention an MDV of strain Rispens (MDV1), strain SB1 (MDV2), or strains FC-126 or PB1 (HVT) is preferred as additional immunoactive component.

To improve the response against NDV, the recombinant npMDV according to the invention may be combined with an NDV vaccine strain such as the mild live NDV vaccine strain C2.

Similarly, to improve the response against IBDV, the recombinant npMDV according to the invention may be combined with a mild live IBDV vaccine strains such as D78, PBG98, Cu-1, ST-12 or 89-03.

As the skilled person will appreciate, these 'combinations' also include vaccination schedules wherein the recombinant npMDV according to the invention and the additional immunoactive component are not applied simultaneous; e.g. the recombinant npMDV may be applied in ovo, and the NDV C2 and/or the IBDV 89-03 strain can be applied at day one.

Therefore, in a more preferred embodiment of the vaccine according to the invention comprising at least one additional immunoactive component, the at least one additional immunoactive component is a micro-organism selected from the group consisting of a vaccine strain from: MDV, NDV and IBDV, or any combination thereof.

More preferably the additional immunoactive component is selected from the group consisting of: MDV Rispens, MDV SB1, NDV C2, IBDV D78 and IBDV 89-03.

The combination vaccine can be made in a variety of ways: by combining of preparations of virus or host cells, or a mixture of these; all are incorporated in the present invention. In a preferred embodiment, the components for such a combination vaccine are conveniently produced separately and then combined and filled into the same vaccine container.

By the methods described above, and exemplified hereinafter, a vaccine according to the invention can be obtained.

Therefore, a further aspect of the invention relates to a method for the preparation of the vaccine according to the invention, said method comprising the steps of:

infecting host cells with a recombinant npMDV according to the invention, harvesting the infected host cells, and admixing the harvested infected host cells with a pharmaceutically acceptable carrier.

Suitable host cells and pharmaceutically acceptable carriers for the invention have been described above. Also, suitable methods for infection, culture and harvesting are well known in the art and are described and exemplified herein.

As outlined above in detail, the recombinant npMDV according to the invention can advantageously be applied in a vaccine for poultry, providing a safe, stable and effective vaccination against MDV, NDV and IBDV, which can be administered to poultry at a very young age.

Therefore, a further aspect of the invention relates to the recombinant npMDV according to the invention, for use in a vaccine for poultry.

The different aspects and embodiments of 'use in a vaccine' have been outlined above and comprise the use as cell-free or as cell-associated virus in different vaccine compositions for inoculation of poultry.

Consequently, the different aspects and embodiments of the invention can advantageously be used to produce a safe, stable and effective vaccine for poultry.

Therefore, in a further aspect, the invention relates to the use of the recombinant npMDV, the nucleic acid molecule, the recombinant DNA molecule, or the host cell, all according to the invention, or any combination thereof, for the manufacture of a vaccine for poultry.

As described above, and as exemplified hereinafter, the vaccine according to the invention can advantageously be used to provide a safe and effective immune protection in poultry to a number of diseases, by a single inoculation at very young age.

Therefore, in a further aspect, the invention relates to a method of vaccination of poultry, comprising the step of inoculating said poultry with a vaccine according to the invention.

Details on the inoculation of poultry with a vaccine according to the invention have been described above; specifically the inoculation by intramuscular or subcutaneous inoculation of day old chicks, and the in ovo inoculation of 18 day old embryos.

The invention will now be further described with reference to the following, non-limiting, examples.

EXAMPLES

1. The Different Expression Cassette-Assemblies Tested:

(see FIG. 1 for graphic representation of the constructs described, and Table 1 for overview of results)

1.1. HVT-F and HVT-VP2:

Two recombinant HVT's had been constructed with single gene expression cassettes; comprising either the NDV clone 30 F protein gene, or the VP2 gene from the classic type IBDV strain Faragher 52/70. The two used different promoters: the F protein gene was driven by the Rous sarcoma virus LTR promoter, and the VP2 gene by an hCMV-IE1 gene core promoter. Both expression cassettes had been introduced (by in vitro homologous recombination) into the Us10 gene of the HVT genome of parent strain PB1. The HVT-F recombinant is the same as that used in the commercial vaccine Innovax™ ND.

Both recombinants performed well with regard to stability, viremia and expression. When these two recombinant HVT's were combined in one inoculation; reisolation of vaccinated chickens after 4 weeks showed that only one of the two could be reisolated in significant numbers, with minor amounts of the other. The mutual exclusion did not always affect the same construct: sometimes HVT-F survived, sometimes HVT-VP2.

Viremia in vivo was determined as the percentage of peripheral blood lymphocytes (PBL) infected with (recombinant) HVT, in blood-samples taken from inoculated chicks at two or three weeks after inoculation.

In vivo protection was determined as follows: NDV protection was measured by scoring surviving chicks after challenge with a lethal dose of virulent NDV virus. IBDV protection was measured by histological determination of lymphocyte depletion in the bursa; the scoring system used runs from a 5 for complete depletion (no protection), to 0 for complete protection (no depletion).

1.2. HVP163:

The recombinant HVT named HVP163, comprised an expression cassette in Us10 of the PB1 HVT strain that is a combination of the two cassettes in the HVT-F and HVT-VP2 recombinants: the IE/VP2 promoter+gene section is upstream of the LTR/F section. A transcription terminator was introduced downstream of the F protein gene, which was derived from the Us/TRs junction of FHV1; the VP2 already had a terminator, that of the hCMV-IE1 gene.

This recombinant performed poorly; no expression of the F protein gene could be detected.

1.3. HVP193:

In the expression cassette for HVP193 the LTR promoter was replaced by a stronger promoter: the chimeric chicken beta-actin gene promoter, as an element of 1.34 kb long, derived from Genbank acc. nr.: AJ575208, by NcoI-EcoRI restriction enzyme digestion.

While expression of both VP2 and F heterologous proteins was clearly detectable, the replication in vivo was poor compared to that of the parent PB1 strain.

This was also reflected by the results of a vaccination challenge test with HVP193, (described in section on HVP204 below), in which of the HVP193 vaccinated chicks only 17% were protected against a lethal NDV challenge infection.

1.4. HVP204:

HVT recombinant HVP204 comprised two further changes over HVP193: the relative order of the VP2 and F protein genes was exchanged, as well as the promoters that drove these genes. In the resulting expression cassette the F protein gene was now located upstream of the VP2 gene, and the F protein gene was now driven by the hCMV-IE1 gene core promoter; the downstream VP2 gene was driven by the (chimeric) beta-actin gene promoter. IFA stainings with VP2- and F-protein specific antibodies confirmed functional expression of both genes in infected monolayers of CEF. Viremia levels were tested in PBL's of vaccinated chickens at 15 or 22 days p.i. Results showed that in vivo replication of HVP204 was much improved over that of HVP193, but did not approach wild type viremia levels.

Protective capacity in vivo was tested, using two individual HVP204 isolates, against lethal challenge with NDV, or severe challenge with IBDV, three weeks post inoculation at day old.

NDV protection by HVP204 was 47%; IBDV protection was almost complete with lesions scores of 0 to 0.5.

However, the genetic stability of HVP205 recombinant HVTs was inadequate, as up to 26% of the recombinants lost the capability to express one of the two heterologous genes after the 10$^{th}$ consecutive cell-culture passage for inserting the expression cassette of HVP216: into the Us2 gene of HVT parent viral strain FC-126 strain, whereby the recombinant was generated by cosmid regeneration. The resulting recombinant HVP309 showed excellent results in tests for replication, expression, genetic stability and vaccination efficacy (see examples below), like HVP216 did.

TABLE 1

Summary of results for the different expression cassettes tested

| rec. HVT vector constructs | | | expression | | vireamia | | challenge prot. | | |
|---|---|---|---|---|---|---|---|---|---|
| | insert 5'-> 3' | locus | F | VP2 | plaques | chickens | NDV | IBDV | Genet. stabil. |
| HVP-F | LTR + F | Us10 | + | x | + | + | >90% | x | + |
| HVP-VP2 | IE + VP2 | Us10 | x | + | + | + | x | 1 | + |
| HVP163 | IE + VP2 -> LTR + F | Us10 | – | – | ± | x | x | x | x |
| HVP193 | IE + VP2 -> β-act + F | Us10 | + | + | + | ± | 17% | x | x |
| HVP204 | IE + F -> β-act + VP2 | Us10 | + | + | + | + | 47% | 0 | 74% |
| HVP216 | IE + F -> core β-act + VP2 | Us10 | + | + | + | ++ | >90% | 0-0.5 | >99% |
| HVP309 | IE + F -> core β-act + VP2 | Us2 | + | + | + | ++ | 95-100% | 0 | 99.7-100% |
| PB1 | none (parent) | x | x | x | + | ++ | – | 4.5 | x |

x not applicable/not tested
LTR RSV LTR promoter
IE hCMV-IE1 core promoter
β-act chicken beta actin gene promoter
F NDV F gene
VP2 classic IBDV VP2 gene 1.5. HVP216:

Surprisingly it was found that a significant adaptation to the Ch beta-actin promoter gave recombinant HVTs that had the required genetic stability while the other properties of replication and expression were maintained (and even improved). The adaptation made to the chimeric chicken β-actin gene promoter as used in HVP193 and HVP204, was the deletion of a large part of the intron, which in this Ch β-actin gene promoter is situated upstream of the start codon. This could conveniently be done by restriction enzyme digestion with Eco47III and NaeI. This resulted in a deletion from the promoter's intron of 675 bp represented by nucleotides 807-1483 from the NcoI-EcoRI fragment, which itself runs from nucleotide 394-1734 (all in respect of the plasmid in Genbank acc. nr.: AJ575208). The resulting core version of the β-actin gene promoter was used to replace the long version in the expression cassette of HVP204, in the Us10 gene locus of PB1 parent strain.

The resulting recombinant HVP216 had the desired genetic stability, and excellent replicative and expression properties: IFA stainings with VP2- and F-specific antibodies confirmed functional expression of both genes from HVP216 virus that had been cell passaged more than 10 times on CEF cell-cultures.

Immune protection by HVP216 was tested in a series of experiments: an IBDV challenge trial used MDA+chicks vaccinated at day-old (sc) and challenged at day 21. Depletion scores demonstrated that PB1 gave no protection (score 4.5), but excellent IBDV challenge protection was provided by: HVT-VP2: 1.0; HVP204: 0; HVP216: 0 and 0.5 (two parallel isolates).

NDV challenge protection was tested at 3 or at 4 weeks after vaccination of SPF chicks: PB1 provided a negligible protection, but HVP216 protected up to 90% of the chicks at 4 weeks p.v.

1.6. HVP309:

HVP309 recombinant HVTs again differ from those of HVP216 in that a different genomic insertion locus was used 2. Transfection by Cosmid Regeneration General methods for transfection, recombination, selection and amplification were essentially as described in Sondermeijer et al., 1993 (supra), and EP 431.668.

The cosmid regeneration for HVP309 was performed essentially as described in WO 93/25665 (e.g. FIG. 8 of that reference). To allow integrations into the Us region of the FC-126 HVT genome, the region covered by the cosmid nr. 378-50 in WO 93/25665, was now provided from three smaller plasmids: pSY640 and 556-60.6, and one transfer plasmid (p435vec9), overlapping these two, and containing the expression cassette in the Us2 gene locus.

Subgenomic clone pSY640 was obtained from cosmid 378-50 which contained the large (29.6 kb) BamHI-A fragment of the HVT FC-126 genome, encoding all of Us and most of the flanking IRs and TRs. This was done by exchanging in the 378-50 insert, the StuI restriction enzyme site in Us2 by a HindIII site. Digestion with HindIII then cuts this section of the HVT genome roughly in half; for pSY640 the section of Us from 1 to 13.7 kb was used that runs from IRs up to the (original) StuI site in Us2. This section of HVT genome was subcloned in a pSP64 vector (Promega).

Subgenomic clone p556-60.6 consists of most of the other part of the 378-50 insert: the region that runs from about 16.4 kb of BamHI-A (in Us6=gD) up to TRs. This section was subcloned into a pBR322 plasmid The middle part of the BamHI-A fragment of 378-50, where Us 2 is located, was not covered by pSY640 and p556-60.6, and is comprised in transfer plasmid p435vec9 with some additional sections from Us, running from Us10 to Us8 (gE) so that it overlaps with pSY640 and p556-60.6, and incorporates the IE/F-βAct/VP2 expression cassette (as described in SEQ ID NO: 7) in the Us2 gene locus. The resulting plasmid called p435vec9 is depicted in FIG. 4.

The set of seven linearised constructs: 4 cosmids and 3 plasmids is transfected all together into CEFs, using a standard $CaCl_2$ transfection protocol; in short: freshly made CEF's are seeded on 10 cm culture plates and incubated at 38°

C. with 5% $CO_2$. For each plate a total amount of 1 μg DNA of cosmids and plasmids were mixed and 150 mM $CaCl_2$ was added dropwise until precipitation was imminent. This mixture was added to the CEF cell suspension on the culture plates, and incubated for 12 hrs. Supernatant was removed and an overlay of 15% Glycerol was added, and kept on the cells for 1 minute. Then this was removed, washed with PBS, and fresh culture medium was added and cells were incubated for 5 days. Next, cells were harvested by trypsinisation and cells from individual plates were each seeded on fresh monolayers of CEF cells in T175 culture flasks and incubated for 2 days. The T175 flask cultures were trypsinised, washed and reseeded in fresh medium without extra CEFs, and incubated for a further 3 days. Next the amplified transfected cells were harvested by trypsinisation, and dilutions of 10^-2 to 10^-4 were plated on 10 cm plates with CEF monolayers and incubated. After incubation until plaques became visible (about 3 days p.i.), the plates were covered with agar, and a number of individual plaques of HVP309 were isolated and amplified on CEFs.

3. Insert Verification

Figure 5:
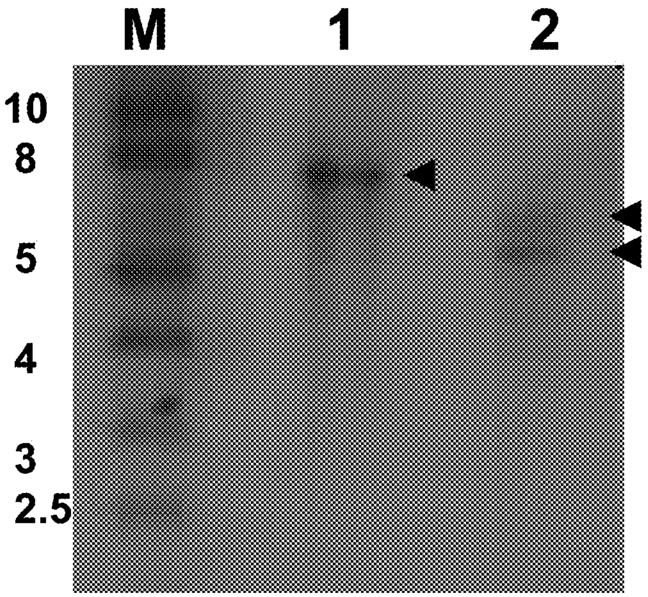

To confirm that the integration of the expression cassette in the HVP309 recombinant HVT had occurred correctly and completely, a variety of verifications were done: a number of individual plaques of HVP309 virus were isolated and amplified in cell-culture. Next these were used for Southern blotting using standard procedures; in short: a gel was run with EcoRI digests of genomic DNA isolated from either the parental HVT FC-126, or the recombinant HVP309. This was blotted on nitrocellulose, and incubated with fragments of the expression cassette that had been labelled with $^{32}P$. An autoradiograph displayed several specific bands: one band of 7.3 kb from FC-126, and two bands from HVP309, of 5.4 and 6.1 kb, see FIG. 5. This proved that HVP309 had integrated the complete expression cassette of about 4.2 kb. Because the probe contained parts from the flanking insertion region, this also confirmed that insertion had occurred at the intended genetic location.

To verify that the 5' and 3' ends of the expression cassette in HVP309 were intact, PCR-sequencing was applied. The upstream Us2 flanking region and the 5'-hCMV-IE1 promoter were detected using PCR primers:

```
                                        (SEQ ID NO: 8)
309F1:      5'-TCACACTAGTTGGGTTTATC-3'

                                        (SEQ ID NO: 9)
309R1:      5'-ACGTAGATGTACTGCCAAGTAG-3'
```

Equally, the 3' end of the VP2 gene and FHV1 transcription terminator with the downstream Us2 flanking region, were detected using PCR primers:

```
                                        (SEQ ID NO: 10)
309F10:      5'-CCGGGCTATAAGGAGGTAAG-3'

                                        (SEQ ID NO: 11)
309R10:      5'-GTACGCGTCCGGGTATACAC-3'.
```

PCR amplification was performed on HVP309 genomic DNA, and both PCR's amplified their expected fragment of about 0.6 kb. PCR reaction was according to manufacturer's recommendation; in short: using Taq™ 2× Master Mix from VWR International, with a program of: 30 sec. 95° C., followed by 30 cycles of: 15 sec. 95° C., 30 sec. 55° C., and 45 sec. 72° C. Finally 5 min. 72° C., and samples were kept at 20° C. until analysis.

The amplicons were purified from agarose gels using the Qiaquick™ kit from Qiagen Inc. Sequencing PCR was performed with the primers described, using the Big Dye™ Terminator v.1.1 Cycle Sequencing kit from Applied Biosystems. The sequencing PCR program was: 10 sec. 94° C., followed by 25 cycles of 5 sec. 50° C. and 2 min. 60° C. Samples were kept at 20° C. until analysis. Unincorporated nucleotides were removed using the Dye Ex™ kit from Qiagen, and sequencing was performed using a 3500 series Genetic Analyzer™ and corresponding software from Applied Biosystems. Sequences were aligned against their reference sequence using Sequencher™ v.4.10.1 software from Gene Codes Corporation.

The sequencing results demonstrated that the 5' and 3' ends of the expression cassette as inserted in HVP309 were correct and complete, as intended, and the insertion locus was indeed in the Us2 gene.

4. Expression Verification by IFA

IFA was performed to verify expression of F and VP2 by HVP309 recombinants, according to standard protocols, in short: CEF were prepared by standard procedure (trypsinisation of 10 ED SPF chicken embryos) and kept in standard culture medium containing 2% FCS, and antibiotics. Each well of a 96 well plate was provided standard medium, and amplified HVP309 isolate, in a 1:5 dilution range. Next CEF cells at 1×10^5/well were added, and plates were incubated for 3 days at 38° C. with 5% $CO_2$. Supernatant was removed, cell monolayer was fixed with 80% ethanol −20° C., for at least 5 minutes. If not stored at −20° C., plates were washed 3× with phosphate based wash buffer. Next, wells were incubated with antibodies, either polyclonal anti NDV or -IBDV, or monoclonal anti-F protein or -VP2 when available. Antibody was used at an appropriate pre-dilution in standard incubation buffer (phosphate wash buffer with Tween 20 and BSA). Plates were Incubated for about 1 hr. at 37° C., washed 3 times, and incubated with an appropriate FITC conjugated second antibody, diluted in incubation buffer, e.g. Goat anti-Mouse IgG-FITC (Sigma, F-0257), at 1:50 dilution. This mixture also contained Evans Blue to counter-stain background cells. After incubation for 1 hr at 37° C., plates were washed 3 times, and wells were covered with glycerol and stored at 4° C. until reading under a UV-microscope.

The isolates from HVP309 showed expression of both F protein and VP 2, from the first plaques after transfection, up until plaques obtained after stability testing through extended cell- and animal passageing.

5. Verification of Genetic Stability After 16 Serial Cell-Culture Passages

Cell-culture passageing and amplification was done by successive passages in primary CEFs. Briefly: primary CEFs were seeded in roller bottles in standard culture medium containing 5% FBS+antibiotics, cultured for 18-24 hours so that monolayers formed, and were infected and incubated. Infected cells were harvested using trypsin when CPE was about 20-50% (typically after 18-25 hours of incubation. Harvested infected CEF cells were then used to infect fresh cells, etc.

To determine the genetic stability of HVP309 isolates, these were subjected to serial cell-culture passages up to $16^{th}$ passage (p16) and then tested for expression of F protein and VP2 by IFA. Two experiments were done with a similar set up: 60 mm plates were seeded with secondary CEF's, and at about 20 hrs post seeding (CEF cells at 80-90% confluency) the plates were infected with p16 HVP309 isolate. At least 10 plates were made for staining F protein, and 10 for staining VP2; each plate having about 10 plaques. Two plates were left uninfected.

After infection, plates were incubated for 5 days. Then total number of plaques was counted on each plate, by light microscopy. Then plates were fixed and IFA stained with F protein or VP2 specific monoclonal antibody, and mouse specific second antibody-FITC conjugate. All plaques on all plates were then inspected, first under bright field microscopy, and next by epi-fluorescence microscopy for fluorescence and thus F protein or VP2 expression.

Results: Trial 1: A total of 344 plaques were inspected by bright field microscopy. Of the 180 plaques stained for VP2 expression, and of the 164 plaques stained for F protein expression, all plaques displayed specific fluorescence, indicating heterologous gene expression at p16.

Trial 2: Of 306 plaques stained for VP2 expression, all were positive; of 326 plaques stained for F protein expression, one plaque (0.3%) did not show expression.

In both trials the non-infected plates did not show any specific fluorescence for either F protein or VP2 expression.

In conclusion: after 16 serial cell culture passages, the level of non-expression from one of the inserted heterologous genes of HVP309 was found to be 0% or 0.3%. This indicates an impressive genetic stability of HVP309.

6. Vaccination-Challenge Test with HVP309 Against IBDV

P16 passaged HVP309 was tested in vaccination-challenge experiments for its remaining capacity to provide an effective immuneprotection against IBDV and NDV (see Example 7).

6.1. Trial Set-Up

Biological products tested: HVP309 at p16; Vaxxitek™ HVT+IBD; and HVT strain FC-126

Animals: SPF white leghorn chickens, at 18 ED. Chicks were wingbanded at hatch, and observed daily, observations noted on symptoms, behaviour, or adverse effects unrelated to the trial. Housed in isolators, and maintained according to standard operating procedures.

Vaccination: in ovo inoculation at 18 ED, with one of the three vaccines tested; administration of 0.1 ml dose into the chorio-allantoic sac, using a 22 G 1.25" needle. Vaccine was back-titrated, and vaccine doses given were about 2000 pfu/dose.

Challenge: Chickens were challenged with classical IBDV strain STC, at 2 or 3 weeks p.v., with about 10^2.5 EID50 per chick, given via in 60 μl volume applied individually by eye-drop.

Observations: respective groups of chickens are tested at 4 days post challenge (p.c.) for macroscopic gross bursa lesions at 4 days p.c., and bursa histology (lymphocyte depletion and lesions) at 10 days p.c.

Data analysis: trial was deemed valid when the unchallenged chickens did not develop disease, whereas more than 70% of the challenged-FC-126 vaccinated chickens developed serious disease.

Evaluation:

positive birds (for challenge virus): were determined by bursa lesion scores: birds were considered positive if they showed any bursal lesion, such as: (peri-bursal) edema, macroscopic hemorrhage, bursa striations or bursal colour change (to yellow/cream colour).

protection (from challenge infection): birds were considered protected when lymphocyte depletion scores were <3, or unprotected at scores between 3-5, on a scale of 0-5.

6.2. Results and Conclusions

The chicks that were vaccinated in ovo with HVT vectored IBDV vaccines Vaxxitek™ HVT+IBD, or HVP309 proved to be well protected against a severe IBDV challenge infection, both at 2 and at 3 weeks post vaccination. Detailed results are presented in Table 2.

6.3. Conclusions

Vaccination with HVP309 recombinant HVT, even after 16 serial cell-passages, provides a very effective immune-protection against a severe challenge with IBDV, as at least 95% of the target animals were protected.

TABLE 2

Results of IBDV challenge infection, by bursa lesions, after vaccination of SPF chicks in ovo with p16 HVP309.

| | vaccine | IBDV STC challenge | | | |
|---|---|---|---|---|---|
| | | 2 weeks pv | | 3 weeks pv | |
| Treatment | titre (pfu/dose) | # positive/total | % protection | # positive/total | % protection |
| HVP309p16 | 1995 | 1/19 | 95 | 0/20 | 100 |
| HVT FC 126 | 1959 | 5/5 | 0 | 5/5 | 0 |

7. Vaccination-Challenge Test with HVP309 Against NDV

In an animal trial, comparable to that of Example 6, the capacity of p12 and p16 HVP309 to protect against NDV was measured. Also this trial compared vaccination in ovo (18 and 19 ED) with day old vaccination.

7.1. Trial Set-Up

Biological products tested: HVP309 at p12 and at p16; Vaxxitek™ HVT-IBD; and Innovax™-ND; placebo: Marek's diluent.

Animals: SPF white leghorn chickens, at 18 or 19 ED, and at day old. Chicks were wingbanded at hatch, and observed daily, observations noted on symptoms, behaviour, or adverse effects unrelated to the trial. Housed in BSL2 class isolators, and maintained according to standard operating procedures.

Vaccination: in ovo inoculation at 18 or 19 ED, with one of the vaccines tested; administration of 0.1 ml dose into the chorio-allantoic sac, using a 22 G 1.25" needle. Day one vaccination was by sc route of 0.2 ml. Vaccine was back-titrated, and vaccine doses given were about 1300 pfu/dose.

Challenge: At time of challenge, vaccinates and controls were commingled in cages. All chickens were challenged with Texas GB strain (velogenic) NDV, at 4 weeks p.v., with about 10^4 EID50 per chick, given in 200 μl volume applied individually by i.m. injection into the breast muscle.

Observations: respective groups of chickens are observed daily for 14 days p.c. for clinical signs of ND.

Data analysis: the trial was deemed valid because more than 90% of the placebo vaccinated-challenged chickens developed clinical signs of ND.

Evaluation: Birds were counted as positive if any clinical signs of NDV were observed, such as any neurological signs or death.

7.2. Results

Both p12 and p16 HVP309 were able to protect chicks against a severe NDV challenge. This was observed both when vaccination was done by in ovo or s.c. route. Only for Innovax™ ND was there effect of the age at which in ovo was applied: 18 or 19 ED.

7.3. Conclusions

Vaccination with HVP309 effectively provided immune-protection in chickens against a severe NDV challenge infection. Both p12 and p16 HVP309 performed equally well. Vaccinations by in ovo route and by sc route at day old performed equally well.

TABLE 3

Results of NDV challenge infection, by NDV clinical signs, after vaccination of SPF chicks in ovo or at day one, with p12 or p16 HVP309.

| Treatment | vaccine titre (pfu/dose) | Route of vacci- nation | Age at vacci- nation | Results of NDV chal- lenge at 4 weeks pv # pos/total | % pro- tection |
|---|---|---|---|---|---|
| HVP309 p12 | 1446 | in ovo | 18 ED | 1/20 | 95 |
| HVP309 p12 | 1158 | in ovo | 19 ED | 1/20 | 95 |
| HVP309 p12 | 1530 | SC | 1 day | 0/19 | 100 |
| HVP309 p16 | 1374 | in ovo | 18 ED | 1/20 | 95 |
| HVP309 p16 | 1410 | in ovo | 19 ED | 0/20 | 100 |
| HVP309 p16 | 2166 | SC | 1 day | 0/19 | 100 |
| Innovax ™-ND | 1428 | in ovo | 18 ED | 1/18 | 94 |
| Marek's diluent | — | in ovo | 18 ED | 10/10 | 0 |

8. Genetic Stability Testing in Vivo

In the course of product development experiments, the recombinant non-pathogenic Marek's disease virus construct HVP309 according to the invention was submitted to repeated animal back-passages to test its stability and safety in vivo in its target animal. To determine safety, chickens inoculated with the passaged recombinant virus were tested for any signs of a reversionto, or an increase of its virulence upon consecutive animal-to-animal passages. To determine genetic stability the virus at the highest animal passage level was compared to the original inoculum before the first animal passage. All experiments were performed according to international guidelines, a short description is given hereafter.

8.1. Animal Passaging

One plaque isolate (called B1) of HVP309 was selected, and amplified into a master seed virus (MSV) preparation by a controlled number of amplification passages on primary CEFs in roller bottles. This MSV material was titrated and used to inoculate one day old SPF leg horn type chickens each with about 50.000 pfu in a 0.2 ml dose, by subcutaneous route. The chickens were healthy, were randomly assigned to the treatment groups, and were kept under isolated conditions; appropriate non-vaccinated controls were included. The birds were kept for 14 days and were monitored closely for any sign of illness or other adverse effects. At 14 days post inoculation, individual blood-samples (3-5 ml) were obtained, and white blood cells were isolated. These were pooled per treatment group and used for plaque titrations and for a further round of animal passaging; the white blood cells were inoculated in new groups of 1 day old chicks, at 0.2 ml by subcutaneous route, and these were also monitored for 14 days. This was repeated for a further 3 rounds, until the MSV had received 5 consecutive animal passages (MSV-AP5).

8.2. General Passage Results

Recombinant virus could be obtained after each animal passage level, as was evident from the results of the intermediary plaque assays after each round. Also, no change of its virulence could be identified, as determined by macroscopic- and microscopic histo-pathological examination of tissues from inoculated and non-inoculated birds after each passage.

8.3. Genetic Stability

The genetic stability of the HVP309B1 recombinant virus was confirmed by isolating and comparing viral DNA from MSV and from MSV-AP5 samples, with respect to the inserted expression cassette and the flanking regions of the insertion site on the HVT viral genome.

Viral genomic DNA was isolated from CEF's that had been inoculated either with the MSV or with white blood cells containing the MSV-AP5 obtained from chickens after the last round of animal passage. The DNA was isolated using standard kits and procedures, and used for a number of PCR reactions (using primers selected at convenient locations, and standard cycling reaction parameters), to amplify out the expression cassette and the flanking regions of the insertion site. This resulted in a set of overlapping fragments of about 600 bp in length, which together spanned a 5.5 kb stretch from the region of interest: the 4.5 kb of the inserted expression cassette, and about 500 bp from each of the flanking regions. DNA sequencing was done using automated cycle-sequencing equipment (Applied Biosystems), and sequence readings were assembled, aligned and analysed using Sequencher® software (Gene Codes Corp.). Some ambiguities in the assembled sequences were resolved by incorporating an additional PCR fragment. A final consensus sequence was assembled for each of the MSV and the MSV-AP5 viral DNA, with a final sequence-reading redundancy of 4-5× per nucleotide.

The consensus sequences of the insert and flanking regions from HVP309B1 virus in MSV and in MSV-AP5 were found to be identical.

This perfect conservation of genetic stability, even after 5 consecutive animal passages, conforms to the results of the phenotypic stability already established in earlier experiments (see Example 5), and demonstrates the very high stability of the HVP309 recombinant virus construct.

LEGEND TO THE FIGURES

FIG. 1:

Graphical representation of the different nucleic acid molecules according to the invention (expression cassettes) tested. Ul and Us: unique long, respectively unique short regions of HVT genome; Us2 and Us 10: genetic insertion locations in the HVT Us2 or Us10 genes; LTR: Rous sarcoma virus long terminal repeat promoter; F: NDV Clone 30 fusion glycoprotein gene; IE: human cytomegalovirus immediate early 1 gene core promoter; IE*: indicates 'core' promoter is used; VP2: infectious bursal disease virus of classic type viral protein 2 gene; small box: transcription terminator-vertical stripes: hCMV-IE1 gene terminator; -horizontal stripes: feline herpesvirus 1 US/TRs junction terminator; β-act.: chicken beta actin gene core promoter, comprising modified splice acceptor site; β-act.*: core promoter used. NB: Elements in FIG. 1 are not drawn to scale. Also, the orientation of the expression cassette relative to the HVT genome can be reversed.

FIG. 2:

Graphical representation of one embodiment of the nucleic acid molecule according to the invention. This corresponds to the 4.5 kb molecule represented in SEQ ID NO: 7. Names and indicators are essentially the same as in FIG. 1.

FIG. 3:

Graphical representation of the protocol for transfection by cosmid regeneration, as used in the assembly of npMDV recombinant HVP309.

The downward pointing triangle indicates the genetic insertion locus; for HVP309 that is Us2.

FIG. 4:

Graphical representation of an embodiment of a recombinant DNA molecule according to the invention; in this case: the p435vec9 transfervector, which was used for the transfection by cosmid regeneration in the assembly of HVP309.

Names and indicators are essentially the same as in FIGS. 1 and 2.

FIG. 5:

Picture from autoradiograph of Southern blot, as described in Example 3. Lanes: M: marker lane with size of bands in kb indicated to the left side of the picture; Lane 1: FC-126 viral DNA digested with EcoRI; Lane 2: HVP309 viral DNA digested with EcoRI. The probe used was insertion vector p435-47, which had been labelled with $^{32}P$. Black triangles indicate the observed bands: lane 1: 7.3 kb; lane 2: 6.1 and 5.4 kb.

The invention claimed is:

1. A recombinant nonpathogenic Marek's disease virus (npMDV) comprising a heterologous nucleic acid molecule, characterised in that the nucleic acid molecule comprises in 5' to 3' direction, and in this order:

a. a human cytomegalovirus immediate early 1 gene (hCMV-IE1) core promoter consisting of SEQ ID NO:1, or a homolog or variant of said hCMV-IE1 core promoter at least 95% identical to SEQ ID NO:1 and 271-451 nucleotides in size,
b. a Newcastle disease virus (NDV) fusion (F) protein gene,
c. a transcription terminator,
d. a an adapted chicken beta-actin gene promoter consisting of SEQ ID NO:4, or a homolog or variant of said adapted promoter at least 95% identical to SEQ ID NO:4and 522-870 nucleotides in size, and
e. a classic type infectious bursal disease virus (IBDV) viral protein 2 (VP2) gene.

2. A nucleic acid molecule for use in the construction of the recombinant npMDV of claim 1, wherein said nucleic acid molecule comprises in 5' to 3' direction, and in this order:

a. an hCMV-IE1 core promoter consisting of SEQ ID NO:1, or a homolog or variant of said hCMV-IE1 core promoter at least 95% identical to SEQ ID NO:1 and 271-451 nucleotides in size,
b. an NDV F protein gene,
c. a transcription terminator,
d. an adapted chicken beta-actin gene core promoter consisting of SEQ ID NO:4, or a homolog or variant of said adapted promoter at least 95% identical to SEQ ID NO:4 and 522-870 nucleotides in size,
e. a classic type IBDV VP2 gene, and
f. a transcription terminator.

3. The recombinant npMDV according to claim 1, wherein the heterologous nucleic acid molecule is inserted into the genome of the recombinant npMDV in the Us region.

4. A method for the preparation of a recombinant npMDV, wherein said method comprises the insertion of the nucleic acid molecule of claim 2 into a single genetic insertion locus on the genome of an npMDV.

5. A host cell comprising the recombinant npMDV of claim 1.

6. A vaccine for poultry comprising the recombinant npMDV of claim 1 and a pharmaceutically acceptable carrier.

7. The vaccine of claim 6, further comprising at least one additional immunoactive component.

8. A method for the preparation of a vaccine for poultry, wherein said method comprises the steps of:

infecting host cells with a recombinant npMDV of claim 1, harvesting the infected host cells, and admixing the harvested infected host cells with a pharmaceutically acceptable carrier.

9. A method of vaccinating a poultry animal, comprising the step of inoculating said poultry animal with the vaccine of claim 6.

10. A method of vaccinating a poultry animal, comprising the step of inoculating said poultry animal with the vaccine of claim 7.

11. A vaccine for poultry comprising the host cell of claim 5, and a pharmaceutically acceptable carrier.

12. The vaccine of claim 11, further comprising at least one additional immunoactive component.

13. A host cell comprising the nucleic acid molecule according to claim 2.

* * * * *